US011174489B2

(12) United States Patent
Pronk et al.

(10) Patent No.: US 11,174,489 B2
(45) Date of Patent: *Nov. 16, 2021

(54) FERMENTATIVE GLYCEROL-FREE ETHANOL PRODUCTION

(71) Applicant: DSM IP Assets B.V., Heerlen (NL)

(72) Inventors: Jacobus Thomas Pronk, Schipluiden (NL); Antonius Jeroen Adriaan Van Maris, Delft (NL); Victor Gabriel Guadalupe Medina, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/176,040

(22) Filed: Feb. 15, 2021

(65) Prior Publication Data

US 2021/0230613 A1 Jul. 29, 2021

Related U.S. Application Data

(63) Continuation of application No. 16/833,342, filed on Mar. 27, 2020, which is a continuation of application No. 15/970,641, filed on May 3, 2018, now Pat. No. 10,738,317, which is a continuation of application No. 15/154,199, filed on May 13, 2016, now abandoned, which is a continuation of application No. 14/189,989, filed on Feb. 25, 2014, now Pat. No. 9,528,117, which is a continuation of application No. 13/061,695, filed as application No. PCT/NL2010/050475 on Jul. 23, 2010, now Pat. No. 8,795,998.

(30) Foreign Application Priority Data

Jul. 24, 2009 (EP) .................................. 09166360

(51) Int. Cl.
| | | |
|---|---|---|
| C12N 15/81 | (2006.01) | |
| C12N 1/18 | (2006.01) | |
| C12N 9/02 | (2006.01) | |
| C12P 7/10 | (2006.01) | |
| C12P 7/06 | (2006.01) | |
| C12N 9/04 | (2006.01) | |
| C12N 9/00 | (2006.01) | |

(52) U.S. Cl.
CPC ............ *C12N 15/815* (2013.01); *C12N 1/18* (2013.01); *C12N 9/0006* (2013.01); *C12N 9/0008* (2013.01); *C12N 9/93* (2013.01); *C12P 7/06* (2013.01); *C12P 7/10* (2013.01); *C12Y 101/01001* (2013.01); *C12Y 101/01008* (2013.01); *C12Y 102/0101* (2013.01); *C12Y 602/01001* (2013.01); *Y02E 50/10* (2013.01); *Y02P 20/52* (2015.11)

(58) Field of Classification Search
None
See application file for complete search history.

(56) References Cited

U.S. PATENT DOCUMENTS

| | | |
|---|---|---|
| 6,476,209 B1 | 11/2002 | Glenn et al. |
| 6,562,958 B1 | 5/2003 | Breton et al. |
| 7,026,463 B2 | 4/2006 | Glenn et al. |
| 7,041,814 B1 | 5/2006 | Weinstock et al. |
| 7,253,001 B2 | 8/2007 | Wahlbom et al. |
| 8,034,591 B2 | 10/2011 | Winker et al. |
| 8,741,652 B2 | 6/2014 | Siddavattam et al. |
| 8,795,998 B2 | 8/2014 | Pronk et al. |
| 9,175,270 B2 | 11/2015 | Nevoigt et al. |
| 9,528,117 B2 | 12/2016 | Pronk et al. |
| 2002/0146721 A1 | 10/2002 | Berka et al. |
| 2005/0153411 A1 | 7/2005 | Wahlbom et al. |
| 2006/0257983 A1 | 11/2006 | Bro et al. |
| 2007/0020625 A1 | 1/2007 | Duchaud et al. |
| 2007/0092957 A1 | 4/2007 | Donaldson et al. |
| 2008/0193470 A1 | 8/2008 | Masignani et al. |
| 2008/0293101 A1 | 11/2008 | Peters et al. |
| 2010/0036174 A1 | 2/2010 | Raamsdonk et al. |
| 2010/0248233 A1 | 9/2010 | Mueller et al. |

(Continued)

FOREIGN PATENT DOCUMENTS

| | | |
|---|---|---|
| JP | 2004159587 A | 6/2004 |
| WO | WO-00/003021 | 1/2000 |
| WO | 2001077334 A2 | 10/2001 |

(Continued)

OTHER PUBLICATIONS

Bellissimi et al., "Effects of acetic acid on the kinetics of xylose fermentation by an engineered, xylose-isomerase-based *Saccharomyces cerevisiae* strain," FEMS Yeast Research (2009) 9(3):358-364.

Cambon et al., "Effects of GPD1 Overexpression in *Saccharomyces cerevisiae* Commercial Wine Yeast Strains Lacking ALD6 Genes," Applied and Environmental Microbiology (2006) 72(7):4688-4694.

Cao et al., "Overexpression of GLT1 in fps1ΔgpdΔ mutant for optimum ethanol formation by *Saccharomyces cerevisiae*," Biomolecular Engineering (2007) 24(6):638-642.

Ehsani et al., "Engineering of 2,3-Butanediol Dehydrogenase To Reduce Acetoin Formation by Glycerol-Overproducing, Low-Alcohol *Saccharomyces cerevisiae*," Applied and Environmental Microbiology (2009) 75(10):3196-3205.

(Continued)

*Primary Examiner* — Kagnew H Gebreyesus
(74) *Attorney, Agent, or Firm* — McBee Moore & Vanik IP, LLC; Susan E. Shaw McBee; Chester G. Moore

(57) ABSTRACT

The present invention relates to a yeast cell, in particular a recombinant yeast cell, the cell lacking enzymatic activity needed for the NADH-dependent glycerol synthesis or the cell having a reduced enzymatic activity with respect to the NADH-dependent glycerol synthesis compared to its corresponding wild-type yeast cell, the cell comprising one or more heterologous nucleic acid sequences encoding an $NAD^+$-dependent acetylating acetaldehyde dehydrogenase (EC 1.2.1.10) activity. The invention further relates to the use of a cell according to the invention in the preparation of ethanol.

30 Claims, 4 Drawing Sheets

Specification includes a Sequence Listing.

(56) References Cited

U.S. PATENT DOCUMENTS

2014/0030730 A1  1/2014  Mueller et al.

FOREIGN PATENT DOCUMENTS

| WO | 2002044383 A1 | 6/2002 |
|---|---|---|
| WO | 03/078643 A1 | 9/2003 |
| WO | WO-2004/048559 | 6/2004 |
| WO | 2004085627 A1 | 10/2004 |
| WO | 2007024718 A2 | 3/2007 |
| WO | 2008052991 A2 | 5/2008 |
| WO | 2009013157 A1 | 1/2009 |
| WO | WO-2009/013159 | 1/2009 |
| WO | 2009056984 A1 | 5/2009 |
| WO | 2009078973 A2 | 6/2009 |
| WO | WO-2009/090050 | 7/2009 |
| WO | WO-2009/111672 | 9/2009 |

OTHER PUBLICATIONS

Ferrandez et al., "Genetic Characterization and Expression in Heterologous Hosts of the 3-(3-Hydroxyphenyl)Propionate Catabolic Pathway of *Escherichia coli* K-12," Journal of Bacteriology (1997) 179(8)2573-2581.

International Search Report for PCT/NL2010/050475, dated Oct. 8, 2010, 5 pages.

Kong et al., "Overexpressing GLT1 in gpd1Δ mutant to improve the production of ethanol of *Saccharomyces cerevisiae*," Applied Microbiology and Biotechnology (2007) 73(6):1382-1386.

Kong et al., "Over-expressing GLT1 in a gpd2Δ mutant of *Saccharomyces cerevisiae* to improve ethanol production," Applied Microbiology and Biotechnology (2007) 75(6):1361-1366.

Lee et al., "Coupled expression of MhpE aldolase and MhpF dehydrogenase in *Escherichia coli*," Biochemical and Biophysical Research Communications (2006) 346(3):1009-1015.

Nielsen, "Metabolic engineering," Applied Microbiology and Biotechnology (2001) 55(3):263-283.

Nissen et al., "Anaerobic and aerobic batch cultivations of *Saccharomyces cerevisiae* mutants impaired in glycerol synthesis," Yeast (2000) 16(5):463-474.

Sonderegger et al., "Metabolic engineering of a Phosphoketolase Pathway for Pentose Catabolism in *Saccharomyces cerevisiae*," Applied and Environmental Microbiology, May 2004, pp. 2892-2897.

Valadi et al., "Improved ethanol production by glycerol-3-phosphate dehydrogenase mutants of *Sachharomyces cerevisiae*," Appl. Microbiol. Biotechnol. (1998) 50:434-439.

Van Maris et al., "Alcoholic fermentation of carbon sources in biomass hydrolysates by *Saccharomyces cerevisiae*: current status," Antonie Van Leeuwenhoek (2006) 90:391-418.

Z. Petek Çakar et al., Evolutionary engineering of *Saccharomyces cerevisiae* for improved industrially important properties, FEMS Yeast Res. 2012, vol. 12, p. 171-182.

Marco Sonderegger et al., Molecular Basis for Anaerobic Growth of *Saccharomyces cerevisiae* on Xylose, Investigated by Global Gene Expression and Metabolic Flux Analysis, Applied and Environmental Microbiology, Apr. 2004, vol. 70, No. 4, p. 2307-2317.

Hidekazu Takahashi et al., Nucleocytosolic Acetyl-Coenzyme A Synthetase Is Required for Histone Acetylation and Global Transcription, Molecular Cell, Jul. 2006, vol. 23, p. 207-217.

Lallemand Invalidity Contentions and Exhibits A, B, C, D, E, F, G, H, Feb. 13, 2017, from Civil Action No. 16-cv-497, West. Dist. Wis. (79 pages).

Guadalupe Medina, Victor et al., "Elimination of Glycerol Production in Anaerobic Cultures of a *Saccharomyces cerevisiae* Strain Engineered To Use Acetic Acid as an Electron Acceptor", Applied and Environmental Microbiology, Jan. 2010, pp. 190-195, vol. 76, No. 1.

Chen, Minghe et al., "Structural analysis of the acetaldehyde dehydrogenase activity of *Entamoeba histolytica* alcohol dehydrogenase 2 (EhADH2), a member of the ADHE enzyme family", Molecular & Biochemical Parasitology, 2004, pp. 201-205, vol. 137.

"Yeast physiology—a key to optimize fermentation process." Proceedings of the Congress—European Brewer Convention (2007), 31st.

Cha, J. et al., "Alocholic hepatotoxicity suppression in alcohol fed rats by glutathione-enriched yeast FF-8 strain", Food Science & Biotechnology, 2009, pp. 1411-1416, vol. 18, No. 6.

Huang, R. et al., "Cloning and expression of acetaldehyde dehydrogenase of *Saccharomyces cerevisiae* W303-1A", Industrial Microbiology, 2009, pp. 22-27 [English abstract], vol. 39, No. 1.

Karhumaa, K. et al., "Proteome analysis of the xylose-fermenting mutant yeast strain TMB 3400", Yeast, 2009, pp. 371-382, vol. 26, No. 7.

Zhao, Y. et al., "Optimization on activity detection system of acetaldehyde dehydrogenase from *Saccharomyces cerevisiae*", China Brewing, 2008, pp. 23-26 [English abstract], vol. 9.

Wang, Y. et al., "Construction of *Saccharomyces cerevisiae* mutant deficient in adh2 and ald6 genes", Microbiology, 2009, pp. 211-216 [Abstract], vol. 36, No. 2.

Shaw, A. et al., "Metabolic engineering of a thermophilic bacterium to produce ethanol at high yield." IPNAS, 2008, pp. 13769-13774, vol. 105, No. 37.

Hu, J. et al., "Mechanism of low nitrogen promoting astaxanthin biosynthesis in *Phaffia rhodozyma*", Journal of Food Science & Biotechnology, 2009, pp. 91-96 [English abstract], vol. 28, No. 1.

Cebollero, E. et al., "Autophagy in wine making", Methods Enzymol, 2008, pp. 163-175 [Abstract], vol. 451.

Albers, E. et al., "Effect of nutrient starvation on the cellular composition and metabolic capacity of *Saccharomyces cerevisiae*", Applied & Environmental Microbiology, 2007, pp. 4839-4848, vol. 73, No. 15.

Frick, O. & C. Wittmann, "Characterization of the metabolic shift between oxidative and fermentative growth in *Saccharomyces cerevisiae* by comparative 13C flux analysis", Microbial Cell Factories, 2005, pp. 1-16, vol. 4, No. 30.

Bro, C. et al., "Genome-wide transcriptional response of a *Saccharomyces cerevisiae* strain with an altered redox metabolism", Biotechnology & Bioengineering, 2004, pp. 269-276 [Abstract], vol. 85, No. 3.

Salusjarvi, L. et al., "Proteome analysis of recombinant xylose-fermenting *Saccharomyces cerevisiae*", Yeast, 2003, pp. 295-314, vol. 20, No. 4.

Wahlbom, C.F. & B. Hahn-Hagerdal, "Furfural, 5-hydroxymethyl furfural, and acetoin act as external electron acceptors during anaerobic fermentation of xylose in recombinant *Saccharomyces cerevisiae*", Biotechnology & Bioengineering, 2002, pp. 172-178 [Abstract], vol. 78, No. 2.

Brejning, J. & L. Jespersen, "Protein expression during lag phase and growth initiation in *Saccharomyces cerevisiae*", International Journal of Food Microbiology, 2002, pp. 27-38 [Abstract], vol. 75(1-2).

Grossmann, M.K. et al., "Effects of enhanced glycerol production on yeast activity and fermentation flavour", Bulletin de l'OIV, 2001, pp. 346-364 [Abstract], vol. 74(843-844).

Urrieta-Saltijeral, J.M. et al., "Metabolic flux modelling as a tool to analyse the behavior of a genetically modified strain of *Saccharomyces cerevisiae*", Focus on Biotechnology, 2001, pp. 143-156 [Abstract], vol. 4, Engineering & Manufacturing for Biotechnology.

Grandier-Vazeille, X. et al., "Yeast mitochondrial dehydrogenases are associated in a supramolecular complex", Biochemistry, 2001, pp. 9758-9769 [Abstract], vol. 40, No. 33.

Segers, G. et al., "Alcohol oxidase is a novel pathogenicity factor for *Cladosporium fulvum*, but aldehyde dehydrogenase is dispensable", Molecular Plant-Microbe Interactions, 2001, pp. 367-377, vol. 14, No. 3.

Remize, F. et al. "Engineering of the pyruvate dehydrogenase bypass in *Saccharomyces cerevisiae*: role of the cytosolic Mg2+ and mitochondrial K+ acetaldehyde dehydrogenases Ald6p and Ald4p in acetate formation during alcoholic fermentation", Applied & Environmental Microbiology, 2000, pp. 3151-3159, vol. 66, No. 8.

(56) References Cited

OTHER PUBLICATIONS

Joubert, R. et al., "Physiological study of the yeast propagation process by 2-D electrophoresis." Monograph—European Brewery Convention, 2000, pp. 171-181, vol. 28, E.B.C.—Symposium Yeast Physiology, 1999.

Boy-Marcotte, E., "Msn2p and Msn4p control a large number of genes induced at the diauxic transition which are repressed by cyclic AMP in *Saccharomyces cerevisiae*", Journal of Bacteriology, 1998, pp. 1044-1052, vol. 180, No. 5.

Waks, Zeev & Pamela A. Silver, "Engineering a Synthetic Dual-Organism System for Hydrogen Production", Applied and Environmental Microbiology, 2009, pp. 1867-1875, vol. 75, No. 7.

Cornelis Verduyn et al., Effect of Benzoic Acid on Metabolic Fluxes in Yeasts: A Continuous-Culture Study on the Regulation of Respiration and Alcoholic Fermentation, Yeast, Feb. 1992, vol. 8, p. 501-517.

Johannes P. Van Dijken et al., Redox balances in metabolism of sugars by yeasts, FEMS Microbiology Reviews, Jan. 1986, Vo. 32, p. 199-224.

Claudio De Virgilio et al., Cloning and Disruption of a Gene Required for Growth on Acetate but not on Ethanol the Acetyl-Coenzyme A Synthetase Gene of *Saccharomyces cerevisiae*, Yeast, Jun. 1992, vol. 8, p. 1043-1051.

Marco A. Van den Berg et al., ACS2, a *Saccharomyces cerevisiae* gene encoding acetyl-coenzyme A synthetase, essential for growth on glucose, Eur. J. Biochem, Apr. 1995, vol. 232, p. 704-713.

Marco A. Van den Berg et al., The Two Acetyl-coenzyme A Synthetases of *Saccharomyces cerevisiae* Differ with Respect to Kinetic Properties and Transcriptional Regulation, The Journal of Biological Chemistry, Nov. 1996, vol. 271, No. 46, p. 28953-28959.

Elke Nevoigt et al., Osmoregulation and glycerol metabolism in the yeast *Saccharomyces cerevisiae*, FEMS Microbiology Reviews, Oct. 1997, vol. 21, p. 231-241.

S. Björkqvist et al., Physiological Response to Anaerobicity of Glycerol-3-Phosphate Dehydrogenase Mutants of *Saccharomyces cerevisiae*, Applied and Environmental Microbiology, Jan. 1997, vol. 63, No. 1, p. 128-132.

Ricky Ansell et al., The two isoenzymes for yeast NAD+-dependent glycerol 3-phosphate dehydrogenase encoded by GPD1 and GPD2 have distinct roles in osmoadaptation and redox regulation, The EMBO Journal, 1997, vol. 16, No. 9, p. 2179-2187.

Sumio Michnick et al., Modulation of Glycerol and Ethanol Yields During Alcoholic Fermentation in *Saccharomyces cerevisiae* Strains Overexpressed or Disrupted for GPD1 Encoding Glycerol 3-Phosphate Dehydrogenase, Yeast, 1997, vol. 13, p. 783-793.

Mohammad J. Taherzadeh et al., Acetic acid-friend or foe in anaerobic batch conversion of glucose to ethanol by *Saccharomyces cerevisiae*?, Chemical Engineering Science, 1997, vol. 52, No. 15, p. 2653-2659.

Karin Athenstaedt et al., Redundant Systems of Phosphatidic Acid Biosynthesis via Acyation of Glycerol-3-Phosphate or Dihydroxyacetone Phosphate in the Yeast *Saccharomyces cerevisiae*, Journal of Bacteriology, Mar. 1999, vol. 181, No. 5, p. 1458-1463.

Karin M. Overkamp et al., In Vivo Analysis of the Mechanisms for Oxidation of Cytosolic NADH by *Saccharomyces cerevisiae* Mitochondria, Journal of Bacteriology, May 2000, vol. 182, No. 10, p. 2823-2830.

Anna-Karin Pahlman et al., The Yeast Glycerol 3-Phosphatases Gpp1p and Gpp2p Are Required for Glycerol Biosynthesis and Differentially Involved in the Cellular Responses to Osmotic, Anaerobic, and Oxidative Stress, The Journal of Biological Chemistry, Feb. 2001, vol. 276, No. 5, p. 3555-3563.

Samira Boubekeur et al., Participation of acetaldehyde dehydrogenases in ethanol and pyruvate metabolism of the yeast *Saccharomyces cerevisiae*, Eur. J. Biochem, Feb. 2001, vol. 268, p. 5057-5065.

Barbara M. Bakker et al., Stoichiometry and compartmentation of NADH metabolism in *Saccharomyces cerevisiae*, FEMS Microbiology Reviews, 2001, vol. 25, p. 15-37.

Karin M. Overkamp et al., Metabolic Engineering of Glycerol Production in *Saccharomyces cerevisiae*, Applied and Environmental Microbiology, Jun. 2002, vol. 68, No. 6, p. 2814-2821.

Garth R. Cronwright et al., Metabolic Control Analysis of Glycerol Synthesis in *Saccharomyces cerevisiae*, Applied and Environmental Microbiology, Sep. 2002, vol. 68, No. 9, p. 4448-4456.

Åsa Valadi et al., Distinct Intracellular Localization of Gpd1p and Gdp2p, the Two Yeast Isoforms of NAD+-dependent Glycerol-3-phosphate Dehydrogenase, Explains Their Different Contributions to Redox-driven Glycerol Production, Sep. 2004, vol. 279, No. 38, p. 39677-39685.

Carine Bideaux et al., Minimization of Glycerol Production during the High-Performance Fed-Batch Ethanolic Fermentation Process in *Saccharomyces cerevisiae*, Using a Metabolic Model as a Prediction Tool, Applied and Environmental Microbiology, Mar. 2006, vol. 72, No. 3, p. 2134-2140.

A. Zhang et al., Effect of FPS1 deletion on the fermentation properties of *Saccharomyces cerevisiae*, Letters in Applied Microbiology, 2006, vol. 44, p. 212-217.

G.N. Vemuri, Increasing NADH oxidation reduces overflow metabolism in *Saccharomyces cerevisiae*, PNAS, Feb. 2007, vol. 104, No. 7, p. 2402-2407.

Zhang Aili et al., Improve Ethanol Yield Through Minimizing Glycerol Yield in Ethanol Fermentation of *Saccharomyces cerevisiae*, Chinese Journal of Chemical Engineering, 2008, vol. 16, No. 4, p. 620-625.

Elke Nevoigt, Progress in Metabolic Engineering of *Saccharomyces cerevisiae*, Microbiology and Molecular Biology Reviews, Sep. 2008, vol. 72, No. 3, p. 379-412.

Zhong-Peng Guo et al., Interruption of glycerol pathway in industrial alcoholic yeasts to improve the ethanol production, Applied Genetics and Molecular Biotechnology, 2009, vol. 82, p. 287-292.

Karyi I. Minard et al., Redox responses in yeast to acetate as the carbon source, Archives of Biochemistry and Biophysics, 2009, vol. 483, p. 136-143.

Frank Vriesekoop et al., The role of acetaldehyde and glycerol in the adaptation to ethanol stress of *Saccharomyces cerevisiae* and other yeasts, FEMS Yeast Res., 2009, vol. 9, p. 365-371.

Derek A. Abbott et al., Metabolic engineering of *Saccharomyces cerevisiae* for production of carboxylic acids: current status and challenges, FEMS Yeast Res., 2009, vol. 9, p. 1123-1136.

SEQUENCE LISTING

<160> NUMBER OF SEQ ID NOS: 32

<210> SEQ ID NO 1
<211> LENGTH: 951
<212> TYPE: DNA
<213> ORGANISM: Escherichia coli
<220> FEATURE:
<221> NAME/KEY: CDS
<222> LOCATION: (1)..(951)

<400> SEQUENCE: 1

| | | | | | | | | | | | | | | | | |
|---|---|---|---|---|---|---|---|---|---|---|---|---|---|---|---|---|
| atg | agt | aag | cgt | aaa | gtc | gcc | att | atc | ggt | tct | ggc | aac | att | ggt | acc | 48 |
| Met | Ser | Lys | Arg | Lys | Val | Ala | Ile | Ile | Gly | Ser | Gly | Asn | Ile | Gly | Thr | |
| 1 | | | | 5 | | | | | 10 | | | | | 15 | | |
| gat | ctg | atg | att | aaa | att | ttg | cgt | cac | ggt | cag | cat | ctg | gag | atg | gcg | 96 |
| Asp | Leu | Met | Ile | Lys | Ile | Leu | Arg | His | Gly | Gln | His | Leu | Glu | Met | Ala | |
| | | | 20 | | | | | 25 | | | | | 30 | | | |
| gtg | atg | gtt | ggc | att | gat | cct | cag | tcc | gac | ggt | ctg | gcg | cgc | gcc | aga | 144 |
| Val | Met | Val | Gly | Ile | Asp | Pro | Gln | Ser | Asp | Gly | Leu | Ala | Arg | Ala | Arg | |
| | | 35 | | | | | 40 | | | | | 45 | | | | |
| cgt | atg | ggc | gtc | gcc | acc | acc | cat | gaa | ggg | gtg | atc | gga | ctg | atg | aac | 192 |
| Arg | Met | Gly | Val | Ala | Thr | Thr | His | Glu | Gly | Val | Ile | Gly | Leu | Met | Asn | |
| | 50 | | | | | 55 | | | | | 60 | | | | | |
| atg | cct | gaa | ttt | gct | gat | atc | gac | att | gta | ttt | gat | gcg | acc | agc | gcc | 240 |
| Met | Pro | Glu | Phe | Ala | Asp | Ile | Asp | Ile | Val | Phe | Asp | Ala | Thr | Ser | Ala | |
| 65 | | | | | 70 | | | | | 75 | | | | | 80 | |
| ggt | gct | cat | gtg | aaa | aac | gat | gcc | gct | tta | cgc | gaa | gcg | aaa | ccg | gat | 288 |
| Gly | Ala | His | Val | Lys | Asn | Asp | Ala | Ala | Leu | Arg | Glu | Ala | Lys | Pro | Asp | |
| | | | | 85 | | | | | 90 | | | | | 95 | | |
| att | cgc | tta | att | gac | ctg | acg | cct | gct | gcc | atc | ggc | cct | tac | tgc | gtg | 336 |
| Ile | Arg | Leu | Ile | Asp | Leu | Thr | Pro | Ala | Ala | Ile | Gly | Pro | Tyr | Cys | Val | |
| | | | 100 | | | | | 105 | | | | | 110 | | | |
| ccg | gtg | gtt | aac | ctc | gag | gcg | aac | gtc | gat | caa | ctg | aac | gtc | aac | atg | 384 |
| Pro | Val | Val | Asn | Leu | Glu | Ala | Asn | Val | Asp | Gln | Leu | Asn | Val | Asn | Met | |
| | | 115 | | | | | 120 | | | | | 125 | | | | |
| gtc | acc | tgc | ggc | ggc | cag | gcc | acc | att | cca | atg | gtg | gcg | gca | gtt | tca | 432 |
| Val | Thr | Cys | Gly | Gly | Gln | Ala | Thr | Ile | Pro | Met | Val | Ala | Ala | Val | Ser | |
| | 130 | | | | | 135 | | | | | 140 | | | | | |
| cgc | gtg | gcg | cgt | gtt | cat | tac | gcc | gaa | att | atc | gct | tct | atc | gcc | agt | 480 |
| Arg | Val | Ala | Arg | Val | His | Tyr | Ala | Glu | Ile | Ile | Ala | Ser | Ile | Ala | Ser | |
| 145 | | | | | 150 | | | | | 155 | | | | | 160 | |
| aaa | tct | gcc | gga | cct | ggc | acg | cgt | gcc | aat | atc | gat | gaa | ttt | acg | gaa | 528 |
| Lys | Ser | Ala | Gly | Pro | Gly | Thr | Arg | Ala | Asn | Ile | Asp | Glu | Phe | Thr | Glu | |
| | | | | 165 | | | | | 170 | | | | | 175 | | |
| acc | act | tcc | cga | gcc | att | gaa | gtg | gtg | ggc | ggc | gcg | gca | aaa | ggg | aag | 576 |
| Thr | Thr | Ser | Arg | Ala | Ile | Glu | Val | Val | Gly | Gly | Ala | Ala | Lys | Gly | Lys | |
| | | | 180 | | | | | 185 | | | | | 190 | | | |
| gcg | att | att | gtg | ctt | aac | cca | gca | gag | cca | ccg | ttg | atg | atg | cgt | gac | 624 |
| Ala | Ile | Ile | Val | Leu | Asn | Pro | Ala | Glu | Pro | Pro | Leu | Met | Met | Arg | Asp | |
| | | 195 | | | | | 200 | | | | | 205 | | | | |
| acg | gtg | tat | gta | ttg | agc | gac | gaa | gct | tca | caa | gat | gat | atc | gaa | gcc | 672 |
| Thr | Val | Tyr | Val | Leu | Ser | Asp | Glu | Ala | Ser | Gln | Asp | Asp | Ile | Glu | Ala | |
| | 210 | | | | | 215 | | | | | 220 | | | | | |
| tca | atc | aat | gaa | atg | gct | gag | gcg | gtg | cag | gct | tac | gta | ccg | ggt | tat | 720 |
| Ser | Ile | Asn | Glu | Met | Ala | Glu | Ala | Val | Gln | Ala | Tyr | Val | Pro | Gly | Tyr | |
| 225 | | | | | 230 | | | | | 235 | | | | | 240 | |
| cgc | ctg | aaa | cag | cgc | gtg | cag | ttt | gaa | gtt | atc | ccg | cag | gat | aaa | ccg | 768 |
| Arg | Leu | Lys | Gln | Arg | Val | Gln | Phe | Glu | Val | Ile | Pro | Gln | Asp | Lys | Pro | |
| | | | | 245 | | | | | 250 | | | | | 255 | | |
| gtc | aat | tta | ccg | ggc | gtg | ggg | caa | ttc | tcc | gga | ctg | aaa | aca | gcg | gtc | 816 |
| Val | Asn | Leu | Pro | Gly | Val | Gly | Gln | Phe | Ser | Gly | Leu | Lys | Thr | Ala | Val | |

```
                         260                 265                 270
tgg ctg gaa gtc gaa ggc gca gcg cat tat ctg cct gcc tat gcg ggc     864
Trp Leu Glu Val Glu Gly Ala Ala His Tyr Leu Pro Ala Tyr Ala Gly
        275                 280                 285 aac ctc gac att atg act tcc agt gcg ctg gcg aca gcg gaa aaa atg     912
Asn Leu Asp Ile Met Thr Ser Ser Ala Leu Ala Thr Ala Glu Lys Met
    290                 295                 300 gcc cag tca ctg gcg cgc aag gca gga gaa gcg gca tga                 951
Ala Gln Ser Leu Ala Arg Lys Ala Gly Glu Ala Ala
305                 310                 315

<210> SEQ ID NO 2
<211> LENGTH: 316
<212> TYPE: PRT
<213> ORGANISM: Escherichia coli

<400> SEQUENCE: 2

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300
```

Ala Gln Ser Leu Ala Arg Lys Ala Gly Glu Ala Ala
305                 310                 315

<210> SEQ ID NO 3
<211> LENGTH: 58
<212> TYPE: DNA
<213> ORGANISM: Artificial
<220> FEATURE:
<223> OTHER INFORMATION: primer

<400> SEQUENCE: 3
ggggacaagt tgtacaaaa aagcaggcta tgagtaagcg taaagtcgcc attatcgg       58

<210> SEQ ID NO 4
<211> LENGTH: 54
<212> TYPE: DNA
<213> ORGANISM: Artificial
<220> FEATURE:
<223> OTHER INFORMATION: primer

<400> SEQUENCE: 4
ggggaccact tgtacaaga aagctgggtg ttcatgccgc ttctcctgcc ttgc           54

<210> SEQ ID NO 5
<211> LENGTH: 64
<212> TYPE: DNA
<213> ORGANISM: Artificial
<220> FEATURE:
<223> OTHER INFORMATION: primer

<400> SEQUENCE: 5
ttgtacaccc cccccctcca caaacacaaa tattgataat ataaacagct gaagcttcgt    60
acgc                                                                64

<210> SEQ ID NO 6
<211> LENGTH: 66
<212> TYPE: DNA
<213> ORGANISM: Artificial
<220> FEATURE:
<223> OTHER INFORMATION: primer

<400> SEQUENCE: 6
aatctaatct tcatgtagat ctaattcttc aatcatgtcc ggcggcatag ccactagtg     60 gatctg                                                              66

<210> SEQ ID NO 7
<211> LENGTH: 65
<212> TYPE: DNA
<213> ORGANISM: Artificial
<220> FEATURE:
<223> OTHER INFORMATION: primer

<400> SEQUENCE: 7
tcaattctct ttcccttttcc ttttccttcg ctcccctccc ttatcccagg ctgaagcttc   60
gtacg                                                               65

<210> SEQ ID NO 8
<211> LENGTH: 66
<212> TYPE: DNA
<213> ORGANISM: Artificial
<220> FEATURE:
<223> OTHER INFORMATION: primer

<400> SEQUENCE: 8

```
gtgtctattc gtcatcgatg tctagctctt caatcatctc cggtaggcat aggccactag    60
tggatc                                                                66
```

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

```
cccacccaca ccaccaatac                                                 20
```

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10

```
cggacgccag atgctagaag                                                 20
```

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11

```
gttcagcagc tcttctctac                                                 20
```

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12

```
ccaaatgcga catgagtcac                                                 20
```

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13

```
cgcacgtcaa gactgtcaag                                                 20
```

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14

```
tcgtatgtga atgctggtcg                                                 20
```

<210> SEQ ID NO 15
<211> LENGTH: 20

```
<212> TYPE: DNA
<213> ORGANISM: Artificial
<220> FEATURE:
<223> OTHER INFORMATION: primer

<400> SEQUENCE: 15
cgcacgtcaa gactgtcaag                                                    20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
tcgtatgtga atgctggtcg                                                    20

<210> SEQ ID NO 17
<211> LENGTH: 2142
<212> TYPE: DNA
<213> ORGANISM: Saccharomyces cerevisiae

<400> SEQUENCE: 17
atgtcgccct ctgccgtaca atcatcaaaa ctagaagaac agtcaagtga aattgacaag        60
ttgaaagcaa aaatgtccca gtctgccgcc actgcgcagc agaagaagga acatgagtat       120
gaacatttga cttcggtcaa gatcgtgcca caacggccca tctcagatag actgcagccc       180
gcaattgcta cccactattc tccacacttg gacgggttgc aggactatca gcgcttgcac       240
aaggagtcta ttgaagaccc tgctaagttc ttcggttcta aagctaccca atttttaaac       300
tggtctaagc cattcgataa ggtgttcatc ccagaccta aaacgggcag gccctccttc        360
cagaacaatg catggttcct caacggccaa ttaaacgcct gttacaactg tgttgacaga       420
catgccttga agactcctaa caagaaagcc attattttcg aaggtgacga gcctggccaa       480
ggctattcca ttacctacaa ggaactactt gaagaagttt gtcaagtggc acaagtgctg       540
acttactcta tgggcgttcg caagggcgat actgttgccg tgtacatgcc tatggtccca       600
gaagcaatca taaccttgtt ggccatttcc cgtatcggtg ccattcactc cgtagtcttt       660
gccgggtttt cttccaactc cttgagagat cgtatcaacg atggggactc taaagttgtc       720
atcactacag atgaatccaa cagaggtggt aaagtcattg agactaaaag aattgttgat       780
gacgcgctaa gagagacccc aggcgtgaga cacgtcttgg tttatagaaa gaccaacaat       840
ccatctgttg ctttccatgc ccccagagat ttggattggg caacagaaaa gaagaaatac       900
aagacctact atccatgcac acccgttgat tctgaggatc cattattctt gttgtatacg       960
tctggttcta ctggtgcccc caagggtgtt caacattcta ccgcaggtta cttgctggga      1020
gctttgttga ccatgcgcta cacttttgac actcaccaag aagacgtttt cttcacagct      1080
ggagacattg ctggattaca aggccacact tatgtggttt atggtccctt actatatggt      1140
tgtgccactt tggtctttga agggactcct gcgtacccaa attactcccg ttattgggat      1200
attattgatg aacacaaagt cacccaattt tatgttgcgc caactgcttt gcgtttgttg      1260
aaaagagctg gtgattccta catcgaaaat cattccttaa atctttgcg ttgcttgggt       1320 tcggtcggtg agccaattgc tgctgaagtt tgggagtggt actctgaaaa aataggtaaa      1380
aatgaaatcc ccattgtaga cacctactgg caaacagaat ctggttcgca tctggtcacc      1440
ccgctggctg gtggtgttac accaatgaaa ccgggttctg cctcattccc cttcttcggt      1500
```

```
attgatgcag ttgttcttga ccctaacact ggtgaagaac ttaacaccag ccacgcagag    1560
ggtgtccttg ccgtcaaagc tgcatggcca tcatttgcaa gaactatttg gaaaaatcat    1620
gataggtatc tagacactta tttgaaccct taccctggct actatttcac tggtgatggt    1680
gctgcaaagg ataaggatgg ttatatctgg attttgggtc gtgtagacga tgtggtgaac    1740
gtctctggtc accgtctgtc taccgctgaa attgaggctg ctattatcga agatccaatt    1800
gtggccgagt gtgctgttgt cggattcaac gatgacttga ctggtcaagc agttgctgca    1860
tttgtggtgt tgaaaaacaa atctagttgg tccaccgcaa cagatgatga attacaagat    1920
atcaagaagc atttggtctt tactgttaga aaagacatcg ggccatttgc cgcaccaaaa    1980
ttgatcattt tagtggatga cttgcccaag acaagatccg gcaaaattat gagacgtatt    2040
ttaagaaaaa tcctagcagg agaaagtgac caactaggcg acgtttctac attgtcaaac    2100
cctggcattg ttagacatct aattgattcg gtcaagttgt aa                       2142

<210> SEQ ID NO 18
<211> LENGTH: 2052
<212> TYPE: DNA
<213> ORGANISM: Saccharomyces cerevisiae

<400> SEQUENCE: 18
atgacaatca aggaacataa agtagtttat gaagctcaca acgtaaaggc tcttaaggct     60
cctcaacatt tttacaacag ccaacccggc aagggttacg ttactgatat gcaacattat    120
caagaaatgt atcaacaatc tatcaatgag ccagaaaaat tctttgataa gatggctaag    180
gaatacttgc attgggatgc tccatacacc aaagttcaat ctggttcatt gaacaatggt    240
gatgttgcat ggttttttgaa cggtaaattg aatgcatcat acaattgtgt tgacagacat    300
gcctttgcta atcccgacaa gccagctttg atctatgaag ctgatgacga atccgacaac    360
aaaatcatca catttggtga attactcaga aaagtttccc aaatcgctgg tgtcttaaaa    420
agctggggcg ttaagaaagg tgacacagtg gctatctatt tgccaatgat ccagaagcg     480 gtcattgcta tgttggctgt ggctcgtatt ggtgctattc actctgttgt ctttgctggg    540
ttctccgctg gttcgttgaa agatcgtgtc gttgacgcta attctaaagt ggtcatcact    600
tgtgatgaag gtaaaagagg tggtaagacc atcaacacta aaaaaattgt tgacgaaggt    660
ttgaacggag tcgatttggt ttcccgtatc ttggttttcc aaagaactgg tactgaaggt    720
attccaatga aggccggtag agattactgg tggcatgagg aggccgctaa gcagagaact    780
tacctacctc ctgttttcatg tgacgctgaa gatcctctat tttattata cacttccggt    840 tccactggtt ctccaaaggg tgtcgttcac actacaggtg gttatttatt aggtgccgct    900
ttaacaacta gatacgtttt tgatattcac ccagaagatg ttctcttcac tgccggtgac    960
gtcggctgga tcacgggtca cacctatgct ctatatggtc cattaacctt gggtaccgcc   1020
tcaataattt tcgaatccac tcctgcctac ccagattatg gtagatattg gagaattatc   1080
caacgtcaca aggctaccca tttctatgtg gctccaactg ctttaagatt aatcaaacgt   1140
gtaggtgaag ccgaaattgc caaatatgac acttcctcat acgtgtctct gggttccgtc   1200
ggtgaaccaa tctctccaga cttatgggaa tggtatcatg aaaaagtggg taacaaaaac   1260
tgtgtcattt gtgacactat gtggcaaaca gagtctggtt ctcatttaat tgctcctttg   1320
gcaggtgctc tccaacaaa acctggttct gctaccgtgc cattctttgg tattaacgct   1380
tgtatcattg accctgttac aggtgtggaa ttagaaggta atgatgtcga aggtgtcctt   1440
gccgttaaat caccatggcc atcaatggct agatctgttt ggaaccacca cgaccgttac   1500
```

```
atggatactt acttgaaacc ttatcctggt cactatttca caggtgatgg tgctggtaga      1560
gatcatgatg ttactactg gatcaggggt agagttgacg acgttgtaaa tgtttccggt      1620
catagattat ccacatcaga aattgaagca tctatctcaa atcacgaaaa cgtctcggaa      1680
gctgctgttg tcggtattcc agatgaattg accggtcaaa ccgtcgttgc atatgtttcc      1740
ctaaaagatg gttatctaca aaacaacgct actgaaggtg atgcagaaca catcacacca      1800
gataatttac gtagagaatt gatcttacaa gttaggggtg agattggtcc tttcgcctca      1860
ccaaaaacca ttattctagt tagagatcta ccaagaacaa ggtcaggaaa gattatgaga      1920
agagttctaa gaaaggttgc ttctaacgaa gccgaacagc taggtgacct aactactttg      1980
gccaacccag aagttgtacc tgccatcatt tctgctgtag agaaccaatt tttctctcaa      2040
aaaaagaaat aa                                                          2052

<210> SEQ ID NO 19
<211> LENGTH: 1047
<212> TYPE: DNA
<213> ORGANISM: Saccharomyces cerevisiae

<400> SEQUENCE: 19
atgtctatcc cagaaactca aaaaggtgtt atcttctacg aatcccacgg taagttggaa       60
tacaaagata ttccagttcc aaagccaaag gccaacgaat tgttgatcaa cgttaaatac      120
tctggtgtct gtcacactga cttgcacgct tggcacggtg actggccatt gccagttaag      180
ctaccattag tcggtggtca cgaaggtgcc ggtgtcgttg tcggcatggg tgaaaacgtt      240
aagggctgga agatcggtga ctacgccggt atcaaatggt tgaacggttc ttgtatggcc      300
tgtgaatact gtgaattggg taacgaatcc aactgtcctc acgctgactt gtctggttac      360
acccacgacg gttcttttcca acaatacgct accgctgacg ctgttcaagc cgctcacatt      420
cctcaaggta ccgacttggc ccaagtcgcc cccatcttgt gtgctggtat caccgtctac      480
aaggctttga gtctgctaa cttgatggcc ggtcactggg ttgctatctc cggtgctgct      540
ggtggtctag gttctttggc tgttcaatac gccaaggcta tgggttacag agtcttgggt      600
attgacggtg gtgaaggtaa ggaagaatta ttcagatcca tcggtggtga agtcttcatt      660
gacttcacta aggaaaagga cattgtcggt gctgttctaa aggccactga cggtggtgct      720
cacggtgtca tcaacgtttc cgtttccgaa gccgctattg aagcttctac cagatacgtt      780
agagctaacg gtaccaccgt tttggtcggt atgccagctg gtgccaagtg ttgttctgat      840
gtcttcaacc aagtcgtcaa gtccatctct attgttggtt cttacgtcgg taacagagct      900
gacaccagag aagctttgga cttcttcgcc agaggtttgg tcaagtctcc aatcaaggtt      960
gtcggcttgt ctaccttgcc agaaatttac gaaaagatgg aaaagggtca aatcgttggt     1020
agatacgttg ttgacacttt ctaaataa                                        1047

<210> SEQ ID NO 20
<211> LENGTH: 1047
<212> TYPE: DNA
<213> ORGANISM: Saccharomyces cerevisiae

<400> SEQUENCE: 20
atgtctattc cagaaactca aaaagccatt atcttctacg aatccaacgg caagttggag       60
cataaggata tcccagttcc aaagccaaag cccaacgaat tgttaatcaa cgtcaagtac      120
tctggtgtct gccacaccga tttgcacgct tggcatggtg actggccatt gccaactaag      180
```

-continued

| | |
|---|---|
| ttaccattag ttggtggtca cgaaggtgcc ggtgtcgttg tcggcatggg tgaaaacgtt | 240 |
| aagggctgga agatcggtga ctacgccggt atcaaatggt tgaacggttc ttgtatggcc | 300 |
| tgtgaatact gtgaattggg taacgaatcc aactgtcctc acgctgactt gtctggttac | 360 |
| acccacgacg gttctttcca agaatacgct accgctgacg ctgttcaagc cgctcacatt | 420 |
| cctcaaggta ctgacttggc tgaagtcgcg ccaatcttgt gtgctggtat caccgtatac | 480 |
| aaggctttga gtctgccaa cttgagagca ggccactggg cggccattc tggtgctgct | 540 |
| ggtggtctag gttctttggc tgttcaatat gctaaggcga tgggttacag agtcttaggt | 600 |
| attgatggtg gtccaggaaa ggaagaattg tttacctcgc tcggtggtga agtattcatc | 660 |
| gacttcacca agagaaggaa cattgttagc gcagtcgtta aggctaccaa cggcggtgcc | 720 |
| cacggtatca tcaatgtttc cgtttccgaa gccgctatcg aagcttctac cagatactgt | 780 |
| agggcgaacg gtactgttgt cttggttggt ttgccagccg gtgcaaagtg ctcctctgat | 840 |
| gtcttcaacc acgttgtcaa gtctatctcc attgtcggct cttacgtggg gaacagagct | 900 |
| gataccagag aagccttaga tttctttgcc agaggtctag tcaagtctcc aataaaggta | 960 |
| gttggcttat ccagttacc agaaatttac gaaaagatgg agaagggcca aattgctggt | 1020 |
| agatacgttt tgacacttc taaataa | 1047 |

<210> SEQ ID NO 21
<211> LENGTH: 1128
<212> TYPE: DNA
<213> ORGANISM: Saccharomyces cerevisiae

<400> SEQUENCE: 21

| | |
|---|---|
| atgttgagaa cgtcaacatt gttcaccagg cgtgtccaac caagcctatt ttctagaaac | 60 |
| attcttagat tgcaatccac agctgcaatc cctaagactc aaaaaggtgt catctttat | 120 |
| gagaataagg ggaagctgca ttacaaagat atccctgtcc ccgagcctaa gccaaatgaa | 180 |
| attttaatca acgttaaata ttctggtgta tgtcacaccg atttacatgc ttggcacggc | 240 |
| gattggccat tacctgttaa actaccatta gtaggtggtc atgaaggtgc tggtgtagtt | 300 |
| gtcaaactag gttccaatgt caagggctgg aaagtcggtg atttagcagg tatcaaatgg | 360 |
| ctgaacggtt cttgtatgac atgcgaattc tgtgaatcag gtcatgaatc aaattgtcca | 420 |
| gatgctgatt tatctggtta cactcatgat ggttcttttc caacaatttgc gaccgctgat | 480 |
| gctattcaag ccgccaaaat tcaacagggt accgacttgg ccgaagtagc cccaatatta | 540 |
| tgtgctggtt ttactgtata taagcacta aaagaggcag acttgaaagc tggtgactgg | 600 |
| gttgccatct ctggtgctgc aggtggcttg ggttccttgg ccgttcaata tgcaactgcg | 660 |
| atgggttaca gagttctagg tattgatgca ggtgaggaaa aggaaaaact tttcaagaaa | 720 |
| ttgggggtg aagtattcat cgactttact aaaacaaaga atatggtttc tgacattcaa | 780 |
| gaagctacca aggtggccc tcatggtgtc attaacgttt ccgtttctga agccgctatt | 840 |
| tctctatcta cggaatatgt tagaccatgt ggtaccgtcg ttttggttgg tttgcccgct | 900 |
| aacgcctacg ttaaatcaga ggtattctct catgtggtga agtccatcaa tatcaagggt | 960 |
| tcttatgttg gtaacagagc tgatacgaga aagccttag acttctttag cagaggtttg | 1020 |
| atcaaatcac caatcaaaat tgttggatta tctgaattac caaaggttta tgacttgatg | 1080 |
| gaaaagggca gattttggg tagatacgtc gtcgatacta gtaaataa | 1128 |

<210> SEQ ID NO 22
<211> LENGTH: 1149

```
<212> TYPE: DNA
<213> ORGANISM: Saccharomyces cerevisiae

<400> SEQUENCE: 22
atgtcttccg ttactgggtt ttacattcca ccaatctctt tctttggtga aggtgcttta      60
gaagaaaccg ctgattacat caaaaacaag gattacaaaa aggctttgat cgttactgat     120
cctggtattg cagctattgg tctctccggt agagtccaaa agatgttgga agaacgtgac     180
ttaaacgttg ctatctatga caaaactcaa ccaaacccaa atattgccaa tgtcacagct     240
ggtttgaagg ttttgaagga acaaaactct gaaattgttg tttccattgg tggtggttct     300
gctcacgaca atgctaaggc cattgcttta ttggctacta acggtgggga aatcggagac     360
tatgaaggtg tcaatcaatc taagaaggct gctttaccac tatttgccat caacactact     420
gctggtactc cttccgaaat gaccagattc actattatct ctaatgaaga aaagaaaatc     480
aagatggcta tcattgacaa caacgtcact ccagctgttg ctgtcaacga tccatctacc     540
atgtttggtt tgccacctgc tttgactgct gctactggtc tagatgcttt gactcactgt     600
atcgaagctt atgtttccac cgcctctaac ccaatcaccg atgcctgtgc tttgaagggt     660
attgatttga tcaatgaaag cttagtcgct gcatacaaag acggtaaaga caagaaggcc     720
agaactgaca tgtgttacgc tgaatacttg gcaggtatgg ctttcaacaa tgcttctcta     780
ggttatgttc atgcccttgc tcatcaactt ggtggtttct accacttgcc tcatggtgtt     840
tgtaacgctg tcttgttgcc tcatgttcaa gaggccaaca tgcaatgtcc aaaggccaag     900
aagagattag gtgaaattgc tttgcatttc ggtgcttctc aagaagatcc agaagaaacc     960
atcaaggctt tgcacgtttt aaacagaacc atgaacattc aagaaacttt gaaagaatta    1020
ggtgttaaaa ccgaagattt tgaaattttg gctgaacacg ccatgcatga tgcctgccat    1080
ttgactaacc cagttcaatt caccaaagaa caagtggttg ccattatcaa gaaagcctat    1140
gaatattaa                                                            1149

<210> SEQ ID NO 23
<211> LENGTH: 1056
<212> TYPE: DNA
<213> ORGANISM: Saccharomyces cerevisiae

<400> SEQUENCE: 23
atgccttcgc aagtcattcc tgaaaaacaa aaggctattg tcttttatga gacagatgga      60
aaattggaat ataaagacgt cacagttccg gaacctaagc ctaacgaaat tttagtccac     120
gttaaatatt ctggtgtttg tcatagtgac ttgcacgcgt ggcacggtga ttggccatttt    180 caattgaaat ttccattaat cggtggtcac gaaggtgctg gtgttgttgt aagttgggga     240
tctaacgtta agggctggaa agtcggtgat tttgcaggta taaaatggtt gaatgggact     300
tgcatgtcct gtgaatattg tgaagtaggt aatgaatctc aatgtcctta tttggatggt     360
actggcttca cacatgatgg tactttttcaa gaatacgcaa ctgccgatgc cgttcaagct     420
gcccatattc caccaaacgt caatcttgct gaagttgccc aatcttgtgt gcaggtatc     480 actgttttata aggcgttgaa aagagccaat gtgataccag ccaatggggt cactatatcc     540
ggtgcatgcg gtgcttggg ttctctggca atccaatacg cccttgctat gggttacagg     600
gtcattggta tcgatggtgg taatgccaag cgaaagttat tgaacaatt aggcggagaa     660 atattcatcg atttcacgga gaaaaaagac attgttggtg ctataataaa ggccactaat     720
ggcggttctc atggagttat taatgtgtct gtttctgaag cagctatcga ggcttctacg     780
```

```
aggtattgta ggcccaatgg tactgtcgtc ctggttggta tgccagctca tgcttactgc    840
aattccgatg ttttcaatca agttgtaaaa tcaatctcca tcgttggatc ttgtgttgga    900
aatagagctg atacaaggga ggctttagat ttcttcgcca gaggtttgat caaatctccg    960
atccacttag ctggcctatc ggatgttcct gaaattttg caaagatgga aaggggtgaa    1020
attgttggta gatatgttgt tgagacttct aaatga                             1056

<210> SEQ ID NO 24
<211> LENGTH: 1176
<212> TYPE: DNA
<213> ORGANISM: Saccharomyces cerevisiae

<400> SEQUENCE: 24
atgtctgctg ctgctgatag attaaactta acttccggcc acttgaatgc tggtagaaag     60
agaagttcct cttctgtttc tttgaaggct gccgaaaagc ctttcaaggt tactgtgatt    120
ggatctggta actggggtac tactattgcc aaggtggttg ccgaaaattg taagggatac    180
ccagaagttt tcgctccaat agtacaaatg tgggtgttcg aagaagagat caatggtgaa    240
aaattgactg aaatcataaa tactagacat caaaacgtga atacttgcc tggcatcact    300 ctacccgaca atttggttgc taatccgac ttgattgatt cagtcaagga tgtcgacatc     360
atcgttttca acattccaca tcaattttg ccccgtatct gtagccaatt gaaaggtcat     420
gttgattcac acgtcagagc tatctcctgt ctaaaggggt tgaagttgg gctaaaggt     480 gtccaattgc tatcctctta catcactgag gaactaggta ttcaatgtgg tgctctatct     540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgatta agaattaga tctacatgaa gattag                              1176

<210> SEQ ID NO 25
<211> LENGTH: 1323
<212> TYPE: DNA
<213> ORGANISM: Saccharomyces cerevisiae

<400> SEQUENCE: 25
atgcttgctg tcagaagatt aacaagatac acattcctta agcgaacgca tccggtgtta     60
tatactcgtc gtgcatataa aattttgcct tcaagatcta ctttcctaag aagatcatta    120
ttacaaacac aactgcactc aaagatgact gctcatacta atatcaaaca gcacaaacac    180
tgtcatgagg accatcctat cagaagatcg gactctgccg tgtcaattgt acatttgaaa    240
cgtgcgccct tcaaggttac agtgattggt tctggtaact ggggaccac catcgccaaa    300 gtcattgcgg aaaacacaga attgcattcc catatcttcg agccagaggt gagaatgtgg    360
gtttttgatg aaaagatcgg cgacgaaaat ctgacggata tcataaatac aagacaccag    420
```

| aacgttaaat atctacccaa tattgacctg ccccataatc tagtggccga tcctgatctt | 480 |
| ttacactcca tcaagggtgc tgacatcctt gttttcaaca tccctcatca attttttacca | 540 |
| aacatagtca aacaattgca aggccacgtg gcccctcatg taagggccat ctcgtgtcta | 600 |
| aaagggttcg agttgggctc caagggtgtg caattgctat cctcctatgt tactgatgag | 660 |
| ttaggaatcc aatgtggcgc actatctggt gcaaacttgg caccggaagt ggccaaggag | 720 |
| cattggtccg aaaccaccgt ggcttaccaa ctaccaaagg attatcaagg tgatggcaag | 780 |
| gatgtagatc ataagatttt gaaattgctg ttccacagac cttacttcca cgtcaatgtc | 840 |
| atcgatgatg ttgctggtat atccattgcc ggtgccttga agaacgtcgt ggcacttgca | 900 |
| tgtggtttcg tagaaggtat gggatggggt aacaatgcct ccgcagccat tcaaaggctg | 960 |
| ggtttaggtg aaattatcaa gttcggtaga atgttttttcc cagaatccaa agtcgagacc | 1020 |
| tactatcaag aatccgctgg tgttgcagat ctgatcacca cctgctcagg cggtagaaac | 1080 |
| gtcaaggttg ccacatacat ggccaagacc ggtaagtcag ccttggaagc agaaaaggaa | 1140 |
| ttgcttaacg gtcaatccgc ccaagggata atcacatgca gagaagttca cgagtggcta | 1200 |
| caaacatgtg agttgaccca agaattccca ttattcgagg cagtctacca gatagtctac | 1260 |
| aacaacgtcc gcatggaaga cctaccggag atgattgaag agctagacat cgatgacgaa | 1320 |
| tag | 1323 |

<210> SEQ ID NO 26
<211> LENGTH: 753
<212> TYPE: DNA
<213> ORGANISM: Saccharomyces cerevisiae

<400> SEQUENCE: 26

| atgcctttga ccacaaaacc tttatctttg aaaatcaacg ccgctctatt cgatgttgac | 60 |
| ggtaccatca tcatctctca accagccatt gctgctttct ggagagattt cggtaaagac | 120 |
| aagccttact tcgatgccga acacgttatt cacatctctc acggttggag aacttacgat | 180 |
| gccattgcca agttcgctcc agactttgct gatgaagaat acgttaacaa gctagaaggt | 240 |
| gaaatcccag aaaagtacgg tgaacactcc atcgaagttc aggtgctgt caagttgtgt | 300 |
| aatgctttga acgccttgcc aaaggaaaaa tgggctgtcg ccacctctgg tacccgtgac | 360 |
| atggccaaga aatggttcga cattttgaag atcaagagac cagaatactt catcaccgcc | 420 |
| aatgatgtca agcaaggtaa gcctcaccca gaaccatact aaagggtag aaacggtttg | 480 |
| ggtttcccaa ttaatgaaca agacccatcc aaatctaagg ttgttgtctt tgaagacgca | 540 |
| ccagctggta ttgctgctgg taaggctgct ggctgtaaaa tcgttggtat tgctaccact | 600 |
| ttcgatttgg acttcttgaa ggaaaagggt tgtgacatca ttgtcaagaa ccacgaatct | 660 |
| atcagagtcg gtgaatacaa cgctgaaacc gatgaagtcg aattgatctt tgatgactac | 720 |
| ttatacgcta aggatgactt gttgaaatgg taa | 753 |

<210> SEQ ID NO 27
<211> LENGTH: 753
<212> TYPE: DNA
<213> ORGANISM: Saccharomyces cerevisiae

<400> SEQUENCE: 27

| atgggattga ctactaaacc tctatctttg aaagttaacg ccgctttgtt cgacgtcgac | 60 |
| ggtaccatta tcatctctca accagccatt gctgcattct ggagggattt cggtaaggac | 120 |

```
aaaccttatt tcgatgctga acacgttatc caagtctcgc atggttggag aacgtttgat    180
gccattgcta agttcgctcc agactttgcc aatgaagagt atgttaacaa attagaagct    240
gaaattccgg tcaagtacgg tgaaaaatcc attgaagtcc aggtgcagt taagctgtgc     300 aacgctttga acgctctacc aaaagagaaa tgggctgtgg caacttccgg tacccgtgat    360
atggcacaaa atggttcga gcatctggga atcaggagac caaagtactt cattaccgct     420
aatgatgtca acagggtaa gcctcatcca gaaccatatc tgaagggcag gaatggctta    480
ggatatccga tcaatgagca agacccttcc aaatctaagg tagtagtatt tgaagacgct    540
ccagcaggta ttgccgccgg aaaagccgcc ggttgtaaga tcattggtat tgccactact    600
ttcgacttgg acttcctaaa ggaaaaaggc tgtgacatca ttgtcaaaaa ccacgaatcc    660
atcagagttg gcggctacaa tgccgaaaca gacgaagttg aattcatttt tgacgactac    720
ttatatgcta aggacgatct gttgaaatgg taa                                753
```

<210> SEQ ID NO 28
<211> LENGTH: 939
<212> TYPE: DNA
<213> ORGANISM: Saccharomyces cerevisiae
<220> FEATURE:
<221> NAME/KEY: CDS
<222> LOCATION: (1)..(939)

<400> SEQUENCE: 28

```
atg aat cag aaa ctg aaa gta gct atc ata ggt tcc ggt aat atc gga     48
Met Asn Gln Lys Leu Lys Val Ala Ile Ile Gly Ser Gly Asn Ile Gly
1               5                   10                  15 aca gac ctg atg att aag gta ctg cgt aat gca aag tac tta gaa atg     96
Thr Asp Leu Met Ile Lys Val Leu Arg Asn Ala Lys Tyr Leu Glu Met
            20                  25                  30 ggc gcg atg gtc ggt atc gat gca gcc tct gat gga ctg gcc aga gct    144
Gly Ala Met Val Gly Ile Asp Ala Ala Ser Asp Gly Leu Ala Arg Ala
        35                  40                  45 caa aga atg ggc gtt acg act act tat gca ggt gta gaa ggg cta atc    192
Gln Arg Met Gly Val Thr Thr Thr Tyr Ala Gly Val Glu Gly Leu Ile
    50                  55                  60 aag ctt cct gaa ttt gca gac ata gat ttc gtc ttc gat gct aca tct    240
Lys Leu Pro Glu Phe Ala Asp Ile Asp Phe Val Phe Asp Ala Thr Ser
65                  70                  75                  80 gca tca gcc cac gtt cag aac gag gct tta tta aga caa gct aaa cct    288
Ala Ser Ala His Val Gln Asn Glu Ala Leu Leu Arg Gln Ala Lys Pro
                85                  90                  95 ggt att aga ttg atc gac ctt acc ccg gcg gca atc ggt cct tac tgt    336
Gly Ile Arg Leu Ile Asp Leu Thr Pro Ala Ala Ile Gly Pro Tyr Cys
            100                 105                 110 gtc ccc gta gtt aat ctc gag gaa cat ttg ggc aag ttg aac gtt aac    384
Val Pro Val Val Asn Leu Glu Glu His Leu Gly Lys Leu Asn Val Asn
        115                 120                 125 atg gtt act tgc ggt ggc caa gct act att ccg atg gtc gca gct gtc    432
Met Val Thr Cys Gly Gly Gln Ala Thr Ile Pro Met Val Ala Ala Val
    130                 135                 140 tca cgt gta gcc aaa gtc cat tat gct gag att gtt gct tct att tca    480
Ser Arg Val Ala Lys Val His Tyr Ala Glu Ile Val Ala Ser Ile Ser
145                 150                 155                 160 agc aag agt gcc gga cct gga acc aga gcc aat ata gat gaa ttc act    528
Ser Lys Ser Ala Gly Pro Gly Thr Arg Ala Asn Ile Asp Glu Phe Thr
                165                 170                 175 gag aca acc agt aaa gcc ata gaa gtt att ggt ggt gct gca aag ggt    576
Glu Thr Thr Ser Lys Ala Ile Glu Val Ile Gly Gly Ala Ala Lys Gly
```

```
                      180                 185                 190
aaa gct ata att att atg aac cca gct gaa cca cca ttg att atg agg          624
Lys Ala Ile Ile Ile Met Asn Pro Ala Glu Pro Pro Leu Ile Met Arg
        195                 200                 205 gat acg gtg tat gtg ctt tcc gcc gcc gct gat caa gcc gct gtc gca          672
Asp Thr Val Tyr Val Leu Ser Ala Ala Ala Asp Gln Ala Ala Val Ala
    210                 215                 220 gct tct gtg gct gaa atg gtt caa gcg gtt caa gca tac gtg cca ggc          720
Ala Ser Val Ala Glu Met Val Gln Ala Val Gln Ala Tyr Val Pro Gly
225                 230                 235                 240 tat agg tta aaa caa cag gtt cag ttt gac gtg att ccc gag tcc gcg          768
Tyr Arg Leu Lys Gln Gln Val Gln Phe Asp Val Ile Pro Glu Ser Ala
                245                 250                 255 cca cta aac atc ccc ggt ttg ggg aga ttc agc ggg ttg aaa aca agt          816
Pro Leu Asn Ile Pro Gly Leu Gly Arg Phe Ser Gly Leu Lys Thr Ser
            260                 265                 270 gtg ttc cta gaa gta gaa ggt gct gct cat tat ttg cca gca tac gca          864
Val Phe Leu Glu Val Glu Gly Ala Ala His Tyr Leu Pro Ala Tyr Ala
        275                 280                 285 gga aac tta gat att atg act tcc gca gcg tta gct aca gcc gaa cgt          912
Gly Asn Leu Asp Ile Met Thr Ser Ala Ala Leu Ala Thr Ala Glu Arg
    290                 295                 300 atg gcg caa tca atg ttg aat gca tag                                      939
Met Ala Gln Ser Met Leu Asn Ala
305                 310

<210> SEQ ID NO 29
<211> LENGTH: 312
<212> TYPE: PRT
<213> ORGANISM: Saccharomyces cerevisiae

<400> SEQUENCE: 29

Met Asn Gln Lys Leu Lys Val Ala Ile Ile Gly Ser Gly Asn Ile Gly
1               5                   10                  15

Thr Asp Leu Met Ile Lys Val Leu Arg Asn Ala Lys Tyr Leu Glu Met
            20                  25                  30

Gly Ala Met Val Gly Ile Asp Ala Ala Ser Asp Gly Leu Ala Arg Ala
        35                  40                  45

Gln Arg Met Gly Val Thr Thr Thr Tyr Ala Gly Val Glu Gly Leu Ile
    50                  55                  60

Lys Leu Pro Glu Phe Ala Asp Ile Asp Phe Val Phe Asp Ala Thr Ser
65                  70                  75                  80

Ala Ser Ala His Val Gln Asn Glu Ala Leu Leu Arg Gln Ala Lys Pro
                85                  90                  95

Gly Ile Arg Leu Ile Asp Leu Thr Pro Ala Ala Ile Gly Pro Tyr Cys
            100                 105                 110

Val Pro Val Val Asn Leu Glu Glu His Leu Gly Lys Leu Asn Val Asn
        115                 120                 125

Met Val Thr Cys Gly Gly Gln Ala Thr Ile Pro Met Val Ala Ala Val
    130                 135                 140

Ser Arg Val Ala Lys Val His Tyr Ala Glu Ile Val Ala Ser Ile Ser
145                 150                 155                 160

Ser Lys Ser Ala Gly Pro Gly Thr Arg Ala Asn Ile Asp Glu Phe Thr
                165                 170                 175

Glu Thr Thr Ser Lys Ala Ile Glu Val Ile Gly Gly Ala Ala Lys Gly
            180                 185                 190

Lys Ala Ile Ile Ile Met Asn Pro Ala Glu Pro Pro Leu Ile Met Arg
```

```
              195                 200                 205
Asp Thr Val Tyr Val Leu Ser Ala Ala Ala Asp Gln Ala Ala Val Ala
            210                 215                 220

Ala Ser Val Ala Glu Met Val Gln Ala Val Gln Ala Tyr Val Pro Gly
225                 230                 235                 240

Tyr Arg Leu Lys Gln Gln Val Gln Phe Asp Val Ile Pro Glu Ser Ala
                245                 250                 255

Pro Leu Asn Ile Pro Gly Leu Gly Arg Phe Ser Gly Leu Lys Thr Ser
            260                 265                 270

Val Phe Leu Glu Val Glu Gly Ala Ala His Tyr Leu Pro Ala Tyr Ala
275                 280                 285

Gly Asn Leu Asp Ile Met Thr Ser Ala Ala Leu Ala Thr Ala Glu Arg
            290                 295                 300

Met Ala Gln Ser Met Leu Asn Ala
305                 310

<210> SEQ ID NO 30
<211> LENGTH: 18
<212> TYPE: DNA
<213> ORGANISM: Artificial
<220> FEATURE:
<223> OTHER INFORMATION: primer

<400> SEQUENCE: 30
cattgattgc gccatacg                                                      18

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
ccggtaatat cggaacagac                                                    20

<210> SEQ ID NO 32
<211> LENGTH: 939
<212> TYPE: DNA
<213> ORGANISM: Pseudomonas sp.

<400> SEQUENCE: 32
atgaaccaga aactcaaagt cgcgatcatc ggttcgggca atatcggcac cgacctgatg        60
atcaaggtgc tgcgcaacgc caagtacctg gaaatgggcg ccatggtcgg catcgacgcc       120
gcctccgacg gcctggcccg cgcccagcgc atgggcgtga cgaccaccta tgccggcgtc       180
gaagggctga tcaagctgcc cgaattcgcc gacatcgatt tcgtcttcga cgccacctcg       240
gccagtgccc acgtgcagaa cgaggcgctg ctgcgccagg ccaaacctgg catccgcctg       300
atcgacctga ccccggcggc catcggcccg tactgcgtgc cggtggtcaa tctggaggag       360
cacctcggca agctcaacgt caacatggtt acctgcggcg gccaggcgac catcccgatg       420
gtcgccgcgg tctcccgtgt ggccaaggtc cattacgccg agatcgtcgc ctcgatcagc       480
agcaagtcgg ccggacccgg cacccgcgcc aacatcgacg agttcaccga gaccaccagc       540
aaagccatcg aagtgatcgg tggtgcggcc aagggcaagg cgatcatcat catgaacccg       600
gctgagccgc cgctgatcat gcgcgacacc gtgtatgtgc tgtccgccgc cgccgatcag       660
gccgccgtcg cggcctcggt ggcggaaatg gttcaggcgg tgcaggccta cgtgcccggc       720
```

```
tatcgcctga agcagcaggt gcagttcgac gtgatccccg agtccgcgcc gctgaacatc    780
cccggtctcg gccggttcag cgggttgaag acctcggtgt tcctcgaagt cgaaggcgcc    840
gcccattacc tgccggccta cgccggcaac ctcgacatca tgacctccgc cgcgctggct    900
accgccgagc gtatggcgca gtcgatgttg aacgcctga                           939
```

FERMENTATIVE GLYCEROL-FREE ETHANOL PRODUCTION

CROSS-REFERENCE TO RELATED APPLICATIONS

This application is a continuation of U.S. Ser. No. 16/833,342, filed 27 Mar. 2020, which is a continuation of U.S. Ser. No. 15/970,641, filed 3 May 2018, now U.S. Pat. No. 10,738,317 which is a continuation of U.S. Ser. No. 15/154,199, filed 13 May 2016, which is a continuation of U.S. Ser. No. 14/189,989, filed 25 Feb. 2014, now U.S. Pat. No. 9,528,117, which is a continuation of U.S. Ser. No. 13/061,695, filed 18 Jul. 2011, now U.S. Pat. No. 8,795,998, which is a national phase of PCT/NL2010/050475, filed 23 Jul. 2010, which claims the benefit of European patent application No. 09166360.9, filed 24 Jul. 2009. The contents of the above patent applications are incorporated by reference herein in their entirety.

SUBMISSION OF SEQUENCE LISTING IN ASCII TEXT FILE

The content of the following submission on ASCII text file is incorporated herein by reference in its entirety: a computer readable form (CRF) of the Sequence Listing (file name: 2919208-306007_Sequence_Listing_ST25.txt date created: 12 Feb. 2021, size: 38,989 bytes).

BACKGROUND OF THE DISCLOSURE

The present invention relates to a recombinant yeast cell having the ability to produce a desired fermentation product, to the construction of said yeast cell by genetic modification and to a process for producing a fermentation product wherein said yeast cell is used.

Ethanol production by *Saccharomyces cerevisiae* is currently, by volume, the single largest fermentation process in industrial biotechnology. A global research effort is underway to expand the substrate range of *S. cerevisiae* to include lignocellulosic hydrolysates, in particular hydrolysed lignocellulosic biomass from non-food feedstocks (e.g. energy crops and agricultural residues, forestry residues or industrial/consumer waste materials that are rich in cellulose, hemicellulose and/or pectin) and to increase productivity, robustness and product yield.

Lignocellulosic biomass is abundant, however is in general not readily fermented by wild-type ethanol producing micro-organisms, such as *S. cerevisiae*. The biomass has to be hydrolysed. The resultant hydrolysate is often a mixture of various monosaccharides and oligosaccharides, which may not all be suitable substrates for the wild-type microorganism. Further, the hydrolysates typically comprise acetic acid, formed as a by-product in particular when hydrolysing pectin or hemicellulose, and—dependent on the type of hydrolysis—one or more other by-products or residual reagents that may adversely affect the fermentation. In particular, acetic acid has been reported to negatively affect the kinetics and/or stoichiometry of sugar fermentation by wild-type and genetically modified *S. cerevisiae* strains and its toxicity is strongly augmented at low culture pH (Helle et al. Enzyme Microb Technol 33 (2003) 786-792; Bellissimi et al. FEMS Yeast Res 9 (2009) 358-364).

Various approaches have been proposed to improve the fermentative properties of ethanol producing organisms by genetic modification, and to improve the hydrolysis process of the biomass. E.g. an overview of developments in the fermentative production of ethanol from biomass hydrolysates is given in a review by A. van Maris et al. (Antonie van Leeuwenhoek (2006) 90:391-418). Reference is made to various ways in which *S. cerevisiae* may be modified and to various methods of hydrolysing lignocellulosic biomass.

A major challenge relating to the stoichiometry of yeast-based ethanol production is that substantial amounts of glycerol are invariably formed as a by-product. It has been estimated that, in typical industrial ethanol processes, up to about 4 wt. % of the sugar feedstock is converted into glycerol (Nissen et al. Yeast 16 (2000) 463-474). Under conditions that are ideal for anaerobic growth, the conversion into glycerol may even be higher, up to about 10%.

Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is reoxidized by converting acetaldehyde, formed by decarboxylation of pyruvate to ethanol via $NAD^+$-dependent alcohol dehydrogenase. The fixed stoichiometry of this redox-neutral dissimilatory pathway causes problems when a net reduction of NAD to NADH occurs elsewhere in metabolism. Under anaerobic conditions, NADH reoxidation in *S. cerevisiae* is strictly dependent on reduction of sugar to glycerol. Glycerol formation is initiated by reduction of the glycolytic intermediate dihydroxyacetone phosphate to glycerol 3-phosphate, a reaction catalyzed by $NAD^+$-dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment.

It is an object of the invention to provide a novel recombinant cell, which is suitable for the anaerobic, fermentative production of ethanol from a carbohydrate, in particular a carbohydrate obtained from lignocellulosic biomass, which has a reduced glycerol production compared to its corresponding wild-type organism or which lacks glycerol production if the cell is used for the fermentative preparation of ethanol.

It is further an object to provide a novel method for fermentatively preparing ethanol in anaerobic yeast cultures, in which method no glycerol is formed, or at least wherein less glycerol is formed than in a method making use of known strains of *S. cerevisiae*.

One or more further objects that may be met are apparent from the description and/or claims.

The inventors have realised that it is possible to meet one or more of these objectives by providing a specific recombinant cell wherein a specific other enzymatic activity has been incorporated, which allows re-oxidation of NADH formed in the fermentation of a carbohydrate, also in the absence of enzymatic activity needed for the NADH-dependent glycerol synthesis.

Accordingly the present invention relates to a recombinant yeast cell, the cell comprising one or more recombinant, in particular one or more heterologous, nucleic acid sequences encoding an $NAD^+$-dependent acetylating acetaldehyde dehydrogenase (EC 1.2.1.10) activity.

The inventors have in particular realised that it is advantageous to provide a cell without enzymatic activity needed for the NADH-dependent glycerol synthesis or a cell with reduced enzymatic activity needed for the NADH-dependent glycerol synthesis.

Accordingly, the invention in particular relates to a recombinant yeast cell comprising one or more heterologous nucleic acid sequences encoding an $NAD^+$-dependent acetylating acetaldehyde dehydrogenase activity, wherein the cell lacks enzymatic activity needed for the NADH-dependent glycerol synthesis (i.e. is free of such activity), or wherein the cell has a reduced enzymatic activity with respect to NADH-dependent glycerol synthesis compared to its corresponding wild-type yeast cell.

The invention is further directed to the use of a cell according to the invention for the preparation of ethanol.

In particular, the invention is further directed to a method for preparing ethanol, comprising preparing ethanol from a fermentable carbohydrate and from acetate, which preparation is carried out under anaerobic fermentative conditions using a yeast cell, said cell expressing acetyl-Coenzyme A synthetase activity and $NAD^+$-dependent acetylating acetaldehyde dehydrogenase activity, said cell preferably lacking enzymatic activity needed for the biochemical pathway for glycerol synthesis from a carbohydrate or having a reduced enzymatic activity with respect to the biochemical pathway for glycerol synthesis from a carbohydrate compared to a wild-type S. cerevisiae cell.

Advantageously, in accordance with the invention ethanol is produced in a molar ratio of glycerol:ethanol of less than 0.04:1, in particular of less than 0.02:1, preferably of less than 0.01:1. Glycerol production may be absent (undetectable), although at least in some embodiments (wherein NADH-dependent glycerol synthesis is reduced yet not completely prohibited) some glycerol may be produced as a side-product, e.g. in a ratio glycerol to ethanol of 0.001:1 or more.

BRIEF DESCRIPTION OF THE DRAWINGS

FIG. 2A: S. cerevisiae IME076 (GPD1 GPD2). FIG. 2B: S. cerevisiae IMZ132 (gpd1Δgpd2Δ overexpressing the E. coli mhpF gene). FIG. 2C: S. cerevisiae IMZ132 (gpd1Δgpd2Δ overexpressing the E. coli mhpF gene). FIG. 2D: S. cerevisiae IMZ127 (gpd1Δgpd2Δ) grown on glucose (20 g·$l^{-1}$).

DETAILED DESCRIPTION OF THE DISCLOSURE

Figure 1:
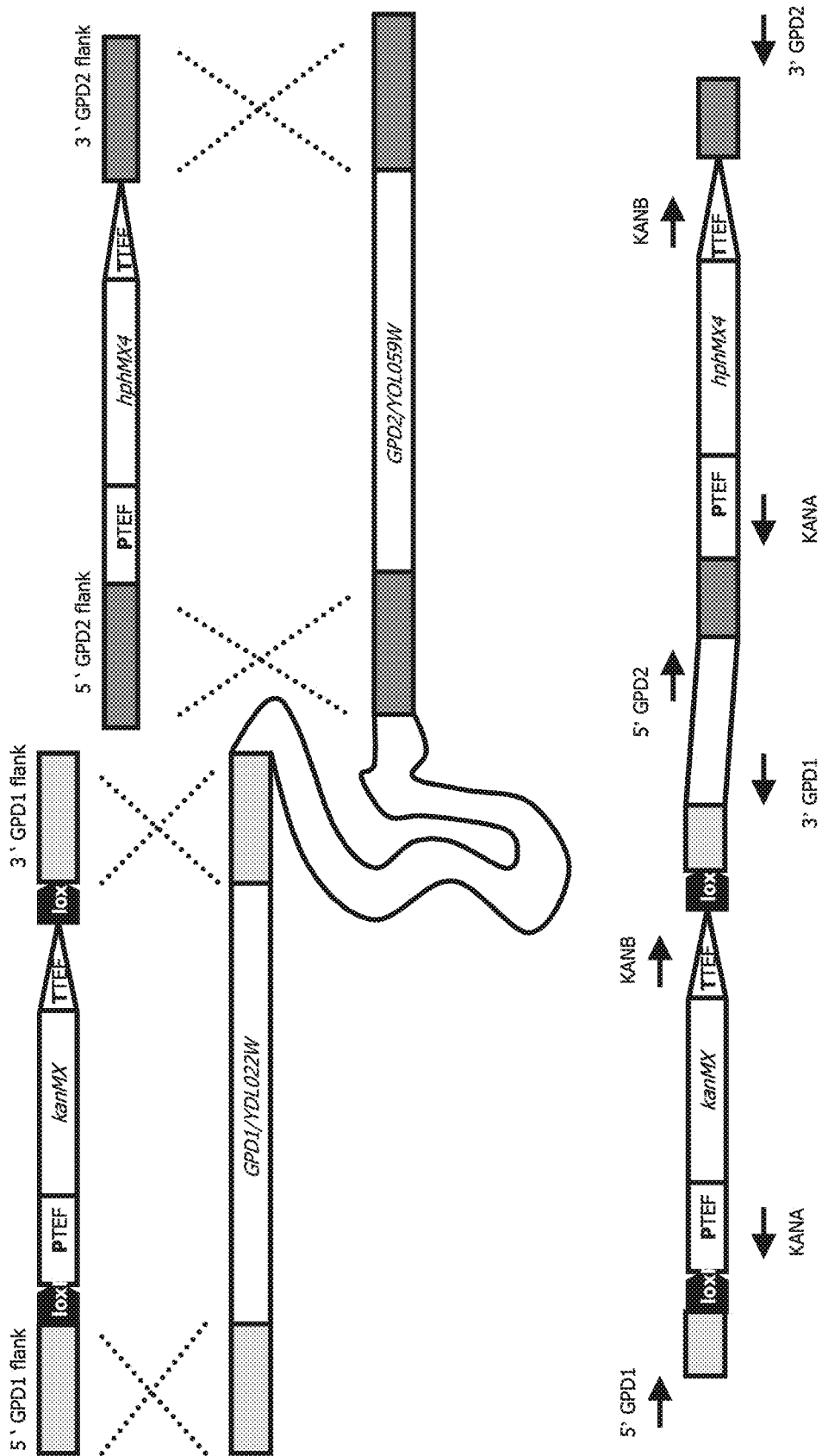
FIG. 1 schematically shows a genetic modification procedure which may be carried out as part of the production of a cell according to the invention.
Figure 2A:
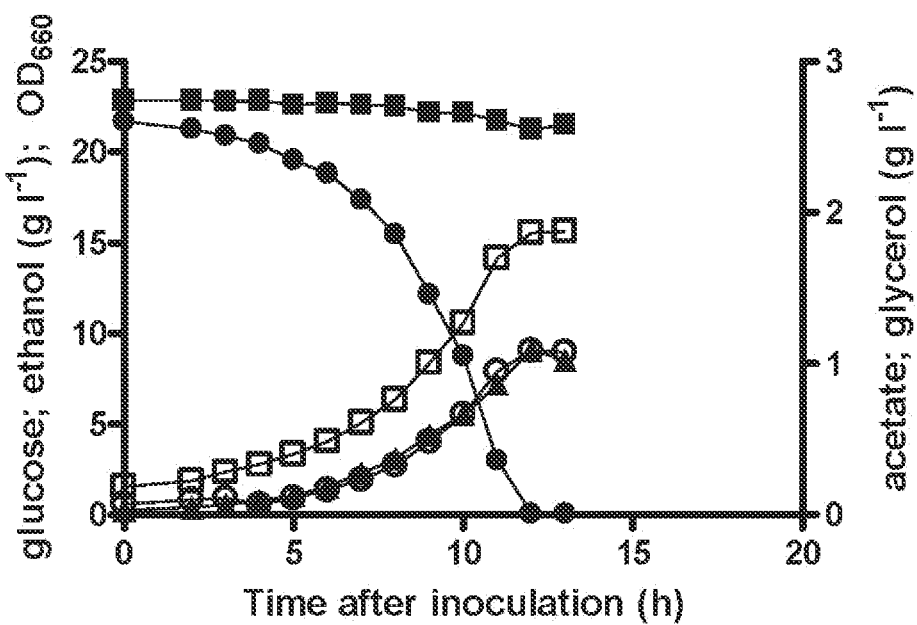
FIGS. 2A-2D show concentrations of biomass and products in anaerobic batch cultures of different S. cerevisiae strains on glucose (20 g $l^{-1}$). Acetic acid (2.0 g $l^{-1}$) was present from the start of the fermentation (panel A, B) or added at the time point indicated by the arrow (panel C, D). Growth conditions: T=30° C., pH 5.0. Symbols: ◇, optical density at 660 nm; ●, glucose; ○, ethanol; ■, acetate; □, glycerol. Each graph represents values from one of two independent replicates, yielding data that differed by less than 5%.
Figure 2B:
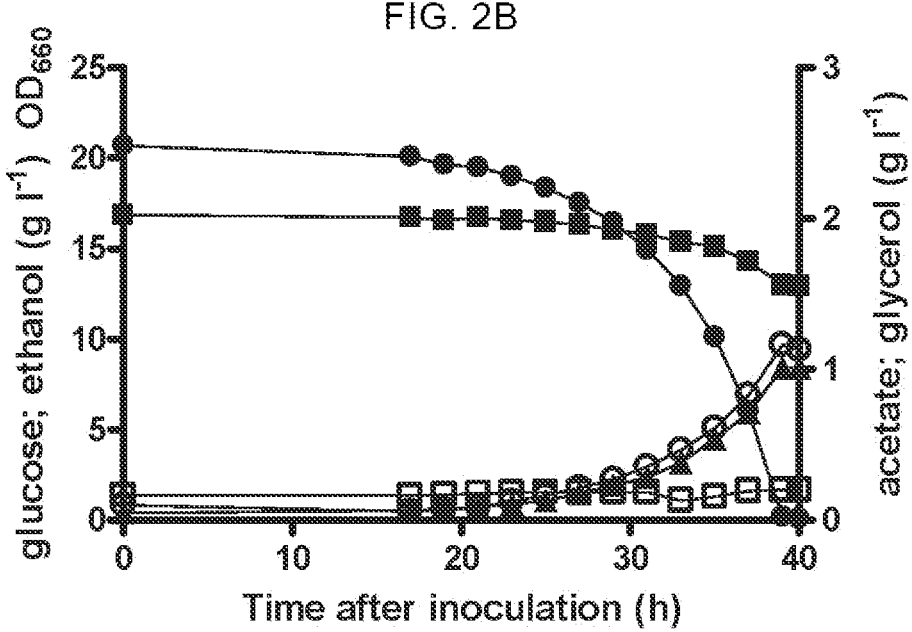
Figure 2C:
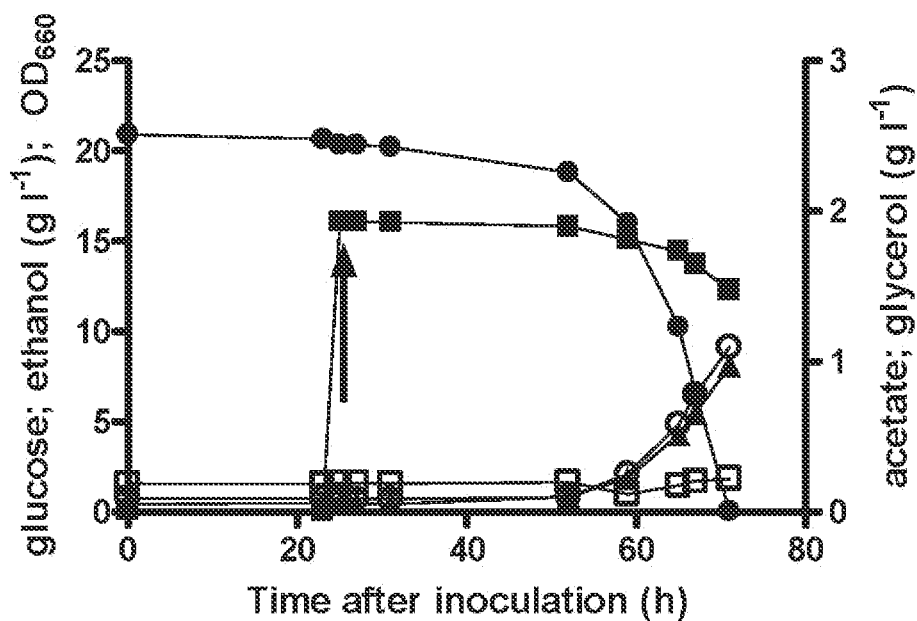
Figure 2D:
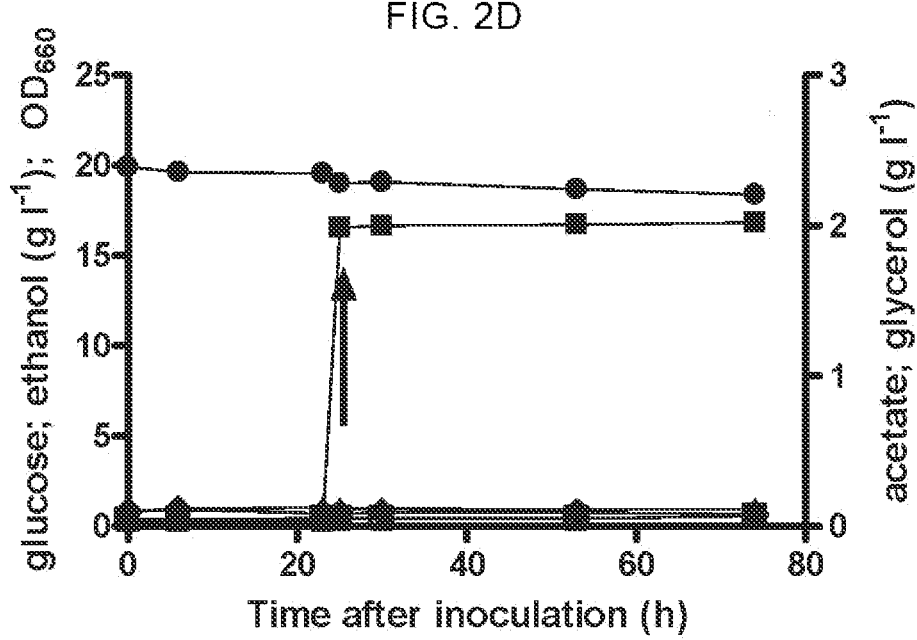

The present invention allows complete elimination of glycerol production, or at least a significant reduction thereof, by providing a recombinant yeast cell, in particular S. cerevisiae, such that it can reoxidise NADH by the reduction of acetic acid to ethanol via NADH-dependent reactions.

This is not only advantageous in that glycerol production is avoided or at least reduced, but since the product formed in the re-oxidation of NADH is also the desired product, namely ethanol, a method of the invention may also offer an increased product yield (determined as the wt. % of converted feedstock, i.e. carbohydrate plus acetic acid, that is converted into ethanol).

Since acetic acid is generally available at significant amounts in lignocellulosic hydrolysates, this makes the present invention particularly advantageous for the preparation of ethanol using lignocellulosic biomass as a source for the fermentable carbohydrate. Further, carbohydrate sources that may contain a considerable amount of acetate include sugar beet molasses (hydrolysates of) and starch containing (e.g. waste products from corn dry milling processes, from corn wet milling processes; from starch wastes processes, e.g. with stillage recycles). The invention contributes to a decrease of the levels of the inhibiting compound acetic acid and a larger fraction of the hydrolysate actually becomes a substrate for the production of the ethanol.

Good results have been achieved with a yeast cell without noticeable enzymatic activity needed for the NADH-dependent glycerol synthesis, as illustrated in the example. However, the inventors contemplate that also a yeast cell according to the invention having NADH-dependent glycerol synthesis activity may advantageously be used for, e.g., ethanol production. It is contemplated that such cell can use acetate to re-oxidise at least part of the NADH. Thereby the acetate may compete with the NADH-dependent glycerol synthesis pathway and thus potentially reduce the glycerol synthesis. Moreover, acetate present in a feedstock used for the production of ethanol, such as a lignocellulosic hydrolysate, can be converted into ethanol, thereby increasing product yield.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "compound", this means "at least one" of that moiety, e.g. "at least one compound", unless specified otherwise.

The term 'or' as used herein is to be understood as 'and/or'.

When referred herein to a carboxylate, e.g. acetate, the corresponding carboxylic acid (its conjugated acid) as well as a salt thereof is meant to be included, and vice versa.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l·h, in particular to an oxygen consumption of less than 2.5 mmol/l·h, or less than 1 mmol/l·h. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant (cell)" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 13 Jul. 2009) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. SEQ ID NO: 2), as used herein, refers to a polypeptide comprising said specific sequence with the proviso that one or more amino acids are substituted, deleted, added, and/or inserted, and which polypeptide has (qualitatively) the same enzymatic functionality for substrate conversion, for instance an NAD+-dependent acetylating acetaldehyde dehydrogenase (EC 1.2.1.10) activity homologue is capable of converting acetaldehyde into ethanol. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99%, for instance having such an amino acid sequence similarity to SEQ ID NO: 2, and having the required enzymatic functionality for converting acetyl-Coenzyme A to acetaldehyde. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected yeast cells may be employed as expression systems for the expression of the enzymes. Expression of heterologous proteins in yeast is well known. Sherman, F., et al., Methods in Yeast Genetics, Cold Spring Harbor Laboratory (1982) is a well recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are cells of the order of Actinomycetales, most preferably yeast cells, most preferably cells of *Saccharomyces cerevisiae*.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

A cell according to the invention preferably is selected from the group of Saccharomycetaceae, more preferably from the group of *Saccharomyces* cells, *Zygosaccharomyces* and *Kluyveromyces* cells. In particular good results have been achieved with a *Saccharomyces cerevisiae* host cell. *Zygosaccharomyces bailii* is another particularly preferred cell, especially for its high acetate tolerance and its high ethanol tolerance.

Further, a cell according to the invention may be a yeast cell selected from the group of xylose-fermenting yeasts, more preferably a *Pichia* species, for example *Pichia stipitis* or *Pichia angusta* (also known as *Hansenula* polymorphs).

In a further embodiment, a host cell according to the invention is a host cell that naturally lacks enzymatic activity needed for the NADH-dependent glycerol synthesis, for example yeast cells belonging to the species *Brettanomyces intermedius*.

A preferred cell according to the invention is free of enzymatic activity needed for the NADH-dependent glycerol synthesis or has a reduced enzymatic activity with respect to the NADH-dependent biochemical pathway for glycerol synthesis from a carbohydrate compared to its corresponding wild-type yeast cell.

A reduced enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encoded a polypeptide with reduced activity. Such modifications can be carried out using commonly known biotechnological techniques, and may in particular include one or more knock-out mutations or site-directed mutagenesis of promoter regions or coding regions of the structural genes encoding GPD and/or GPP. Alternatively, yeast strains that are defective in glycerol production may be obtained by random mutagenesis followed by selection of strains with reduced or absent activity of GPD and/or GPP. *S. cerevisiae* GDP 1, GDP2, GPP1 and GPP2 genes are shown in SEQ ID NO: 24-27.

Preferably at least one gene encoding a GPD or at least one gene encoding a GPP is entirely deleted, or at least a part of the gene is deleted that encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in *Saccharomyces cerevisiae* by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

As indicated above, a cell according to the invention comprises a heterologous nucleic acid sequence encoding an NAD$^+$-dependent, acetylating acetaldehyde dehydrogenase (EC 1.2.1.10). This enzyme catalyses the conversion of acetyl-Coenzyme A to acetaldehyde. This conversion can be represented by the equilibrium reaction formula:

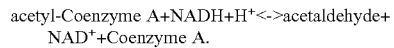

acetyl-Coenzyme A+NADH+H$^+$<->acetaldehyde+ NAD$^+$+Coenzyme A.

Thus, this enzyme allows the re-oxidation of NADH when acetyl-Coenzyme A is generated from acetate present in the growth medium, and thereby glycerol synthesis is no longer needed for redox cofactor balancing.

The nucleic acid sequence encoding the NAD$^+$-dependent acetylating acetaldehyde dehydrogenase may in principle originate from any organism comprising a nucleic acid sequence encoding said dehydrogenase.

Known NAD$^+$-dependent acetylating acetaldehyde dehydrogenases that can catalyse the NADH-dependent reduction of acetyl-Coenzyme A to acetaldehyde may in general be divided in three types of NAD$^+$-dependent acetylating acetaldehyde dehydrogenase functional homologues:

1) Bifunctional proteins that catalyse the reversible conversion of acetyl-Coenzyme A to acetaldehyde, and the subsequent reversible conversion of acetaldehyde to ethanol. An example of this type of proteins is the AdhE protein in *E. coli* (Gen Bank No: NP_415757). AdhE appears to be the evolutionary product of a gene fusion. The NH$_2$-terminal region of the AdhE protein is highly homologous to aldehyde:NAD$^+$ oxidoreductases, whereas the COOH-terminal region is homologous to a family of Fe$^{2+}$-dependent ethanol:NAD$^+$ oxidoreductases (Membrillo-Hernandez et al., (2000) J. Biol. Chem. 275: 33869-33875). The *E. coli* AdhE is subject to metal-catalyzed oxidation and therefore oxygen-sensitive (Tamarit et al. (1998) J. Biol. Chem. 273:3027-32).

2) Proteins that catalyse the reversible conversion of acetyl-Coenzyme A to acetaldehyde in strictly or facultative anaerobic micro-organisms but do not possess alcohol dehydrogenase activity. An example of this type of proteins has been reported in *Clostridium kluyveri* (Smith et al. (1980) Arch. Biochem. Biophys. 203: 663-675). An acetylating acetaldehyde dehydrogenase has been annotated in the genome of *Clostridium kluyveri* DSM 555 (GenBank No:

EDK33116). A homologous protein AcdH is identified in the genome of *Lactobacillus plantarum* (GenBank No: NP_784141). Another example of this type of proteins is the said gene product in *Clostridium beijerinckii* NRRL B593 (Toth et al. (1999) Appl. Environ. Microbiol. 65: 4973-4980, GenBank No: AAD31841).

3) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) Biodegradation 5, 219-236). 4-Hydroxy-2-ketovalerate is first converted by 4-hydroxy-2-ketovalerate aldolase to pyruvate and acetaldehyde, subsequently acetaldehyde is converted by acetylating acetaldehyde dehydrogenase to acetyl-CoA. An example of this type of acetylating acetaldehyde dehydrogenase is the DmpF protein in *Pseudomonas* sp CF600 (GenBank No: CAA43226) (Shingler et al. (1992) J. Bacteriol. 174:71 1-24). The *E. coli* MphF protein (Ferrandez et al. (1997) J. Bacteriol. 179: 2573-2581, GenBank No: NP_414885) is homologous to the DmpF protein in *Pseudomonas* sp. CF600.

A suitable nucleic acid sequence may in particular be found in an organism selected from the group of *Escherichia*, in particular *E. coli*; *Mycobacterium*, in particular *Mycobacterium marinum, Mycobacterium ulcerans, Mycobacterium tuberculosis*; *Carboxydothermus*, in particular *Carboxydothermus hydrogenoformans*; *Entamoeba*, in particular *Entamoeba histolytica*; *Shigella*, in particular *Shigella sonnei*; *Burkholderia*, in particular *Burkholderia pseudomallei*, *Klebsiella*, in particular *Klebsiella pneumoniae*; *Azotobacter*, in particular *Azotobacter vinelandii*; *Azoarcus* sp; *Cupriavidus*, in particular *Cupriavidus taiwanensis*; *Pseudomonas*, in particular *Pseudomonas* sp. CF600; *Pelomaculum*, in particular *Pelotomaculum thermopropionicum*. Preferably, the nucleic acid sequence encoding the NAD$^+$-dependent acetylating acetaldehyde dehydrogenase originates from *Escherichia*, more preferably from *E. coli*.

Particularly suitable is an mhpF gene from *E. coli*, or a functional homologue thereof. This gene is described in Ferrández et al. (1997) J. Bacteriol. 179:2573-2581. Good results have been obtained with *S. cerevisiae*, wherein an mhpF gene from *E. coli* has been incorporated.

In a further advantageous embodiment the nucleic acid sequence encoding an (acetylating) acetaldehyde dehydrogenase is from, in particular *Pseudomonas*. dmpF from *Pseudomonas* sp. CF600.

In principle, the nucleic acid sequence encoding the NAD$^+$-dependent, acetylating acetaldehyde dehydrogenase may be a wild type nucleic acid sequence.

A preferred nucleic acid sequence encodes the NAD$^+$-dependent, acetylating acetaldehyde dehydrogenase represented by SEQ ID NO: 2, SEQ ID NO: 29, or a functional homologue of SEQ ID NO: 2 or SEQ ID NO: 29. In particular the nucleic acid sequence comprises a sequence according to SEQ ID NO: 1. SEQ ID NO: 28 or a functional homologue of SEQ ID NO: 1 or SEQ ID NO: 28.

Further, an acetylating acetaldehyde dehydrogenase (or nucleic acid sequence encoding such activity) may in for instance be selected from the group of *Escherichia coli* adhE, *Entamoeba histolytica* adh2, *Staphylococcus aureus* adhE, *Piromyces* sp.E2 adhE, *Clostridium kluyveri* EDK33116, *Lactobacillus plantarum* acdH, and *Pseudomonas putida* YP 001268189. For sequences of these enzymes, nucleic acid sequences encoding these enzymes and methodology to incorporate the nucleic acid sequence into a host cell, reference is made to WO 2009/013159, in particular Example 3, Table 1 (page 26) and the Sequence ID numbers mentioned therein, of which publication Table 1 and the sequences represented by the Sequence ID numbers mentioned in said Table are incorporated herein by reference.

Usually, a cell according to the invention also comprises an acetyl-Coenzyme A synthetase, which enzyme catalyses the formation of acetyl-coenzyme A from acetate. This enzyme may be present in the wild-type cell, as is for instance the case with *S. cerevisiae* which contains two acetyl-Coenzyme A synthetase isoenzymes encoded by the ACS1 [SEQ ID NO: 17] and ACS2 [SEQ ID NO: 18] genes (van den Berg et al (1996) J. Biol. Chem. 271:28953-28959), or a host cell may be provided with one or more heterologous gene(s) encoding this activity, e.g. the ACS1 and/or ACS2 gene of *S. cerevisiae* or a functional homologue thereof may be incorporated into a cell lacking acetyl-Coenzyme A synthetase isoenzyme activity.

Further, in particular in view of an efficient ethanol production, but also for an efficient NADH oxidation, it is preferred that the cell comprises an NAD$^+$-dependent alcohol dehydrogenase (EC 1.1.1.1). This enzyme catalyses the conversion of acetaldehyde into ethanol. The cell may naturally comprise a gene encoding such a dehydrogenase, as is de case with *S. cerevisiae* (ADH1-5) [SEQ ID NO: 19-23], see 'Lutstorf and Megnet. 1968 Arch. Biochem. Biophys. 126:933-944', or Viriacy, 1975, Mutat. Res. 29:315-326'), or a host cell may be provided with one or more heterologous gene(s) encoding this activity, e.g. any or each of the ADH1-5 genes of *S. cerevisiae* or functional homologues thereof may be incorporated into a cell lacking NAD$^+$-dependent alcohol dehydrogenase activity.

Specifically preferred cells according to the invention are cells of the *S. cerevisiae* strain deposited on 16 Jul. 2009 at the Centraalbureau voor Schimmelcultures (Utrecht, the Netherlands) having deposit number CBS125049.

In specific aspect, the present invention is directed to a method of preparing a recombinant yeast cell according to the invention.

The genetic modification of a cell, comprising the incorporation of one or more heterologous nucleic acid sequences into a host cell, and usually comprising mutation (including complete deletion) of a gene encoding an enzymatic activity needed for the NADH-dependent glycerol synthesis, can be based on common general knowledge, e.g. by standard genetic and molecular biology techniques as generally known in the art and have been previously described (e.g. Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al., eds., "Current protocols in molecular biology", Green Publishing and Wiley Interscience, New York 1987).

A method of the invention for preparing a recombinant yeast cell according to the invention, comprising
(a) providing a yeast cell, preferably a yeast cell selected from the group of yeast cells lacking enzymatic activity needed for the NADH-dependent glycerol synthesis and yeast cell having a reduced enzymatic activity with respect to glycerol synthesis compared to its corresponding wild-type yeast cell;
(b) obtaining a nucleic acid segment comprising a gene that is heterologous to said yeast cell and encodes an enzyme that has NAD$^+$-dependent acetylating acetaldehyde dehydrogenase activity, and wherein said gene is operably linked to a promoter functional in said yeast cell;

(c) if desired (e.g. if the yeast cell lacks acetyl-Coenzyme A synthetase activity or in which the activity of acetyl-Coenzyme A synthetase(s) is limiting the overall in vivo activity of the pathway for conversion of acetate into ethanol or expresses acetyl-Coenzyme A synthetase in a cellular compartment that is not compatible with its use in the invention), obtaining a nucleic acid segment comprising a gene that is heterologous to said yeast cell and encodes an enzyme that has an acetyl-Coenzyme A synthetase activity, and wherein said gene is operably linked to a promoter functional in said yeast cell;

(d) if desired (e.g. if the yeast cell lacks NAD$^+$-dependent alcohol dehydrogenase activity or in which NAD$^+$-dependent alcohol dehydrogenase activity is limiting the in vivo activity of the pathway for conversion of acetate into ethanol or expresses NAD$^+$-dependent alcohol dehydrogenase in a cellular compartment that is not compatible with its use in the invention), obtaining a nucleic acid segment comprising a gene that is heterologous to said yeast cell and encodes an enzyme that has an NAD$^+$-dependent alcohol dehydrogenase activity, and wherein said gene is operably linked to a promoter functional in said yeast cell; and (e) transforming a yeast cell with said nucleic acid segment or segments thereby providing a recombinant yeast cell which expresses said heterologous gene and wherein said recombinant yeast cell exhibits reduced NADH-dependent glycerol synthesis under fermentative conditions as compared to a corresponding non-recombinant yeast cell or wherein in said yeast cell NADH-dependent glycerol synthesis under fermentative conditions is absent.

Promoters for yeast cells are known in the art and can be, for example, the triosephosphate dehydrogenase TPI1 promoters, glyceraldehyde-3-phosphate dehydrogenase TDH3 promoters, translational elongation factor EF-1 alpha TEF1 promoters, the alcohol dehydrogenase ADH1 promoters, glucose-6-phosphate dehydrogenase gpdA and ZWF1 promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, etc or any other, and can be found among others at the NCBI website (ncbi.nlm.nih.gov/entrez).

In a preferred embodiment, the heterologous nucleic acid sequence to be introduced into a yeast cell when preparing a recombinant yeast cell of the invention, is incorporated into a vector, and the transformation of the cell is carried out with the vector. If more than one heterologous nucleic acid sequence (encoding different enzymatic activities or together encoding a single enzymatic activity) are to be incorporated, these nucleic acid sequences may be present in a single vector or these nucleic acid sequences may be incorporated as part of separate vectors.

Accordingly, the invention is further directed to a vector for the expression of a heterologous polypeptide in a yeast cell, in particular a yeast cell, said expression vector comprising one or more heterologous nucleic acid sequences operably linked to a promoter functional in the yeast cell and said heterologous nucleic acid sequence(s) encoding a polypeptide having enzymatic activity for converting acetyl-Coenzyme A into acetaldehyde in (the cytosol of) said yeast cell, wherein said polypeptide preferably comprises a sequence according to SEQ ID NO: 2 or a functional homologue thereof.

The vector (used in a method of) the invention may be a phage vector, a bacterial vector, a centromeric, episomal or integrating plasmid vector or a viral vector.

In a preferred embodiment the vector is a vector for expression in Saccharomyces, in particular S. cerevisiae. In such embodiment, the heterologous nucleic acid sequence encoding NAD$^+$-dependent acetylating acetaldehyde dehydrogenase activity may be codon(-pair) optimised for expression in Saccharomyces, in particular S. cerevisiae, although good results have been achieved with a wild-type encoding nucleic acid sequence.

In order to achieve optimal expression in a specific cell (such as S. cerevisiae), the codon (pair) usage of the heterologous gene may be optimized by using any one of a variety of synthetic gene design software packages, for instance GeneOptimizer® from Geneart AG (Regensburg, Germany) for codon usage optimization or codon pair usage optimization as described in PCT/EP2007/05594. Such adaptation of codon usage ensures that the heterologous genes, which are for instance of bacterial origin, are effectively processed by the yeast transcription and translation machinery. Optimisation of codon pair usage will result in enhanced protein expression in the yeast cell. The optimised sequences may for instance be cloned into a high copy yeast expression plasmid, operably linked to a (preferably constitutive) promoter functional in a fungus (yeast).

As indicated above, the invention is further directed to the preparation of ethanol.

For a method of preparing ethanol, a cell according to the invention is used which under anaerobic conditions ferments a sugar thereby forming ethanol Suitable yeast cells for fermenting the sugar are generally known and include amongst others S. cerevisiae. In a method of the invention, a yeast cell is used that also produces an NAD-dependent acetylating acetaldehyde dehydrogenase (EC 1.2.1.10). This cell can be obtained as described above, and illustrated in the example herein below. If used for the preparation of ethanol, the cell preferably also includes an acetyl-Coenzyme A synthetase activity. If used for the preparation of ethanol, the cell preferably also includes an NAD$^+$-dependent alcohol dehydrogenase activity. These activities may be naturally present, as in S. cerevisiae, or provided by genetic modification (see also herein above).

The fermentation conditions can in principle be based on generally known conditions, e.g. as described in the review by Van Maris cited above, or the references cited therein, with the proviso that typically the medium wherein the fermentation is carried comprises acetate in addition to the fermentable carbohydrate(s).

The molar ratio acetate to carbohydrate consumed by anaerobic cultures of the yeast cells modified according to the invention is usually at least 0.004, in particular at least 0.01, at least 0.03, at least 0.1, or at least 0.2. The molar ratio acetate to carbohydrate present in hydrolysates of lignocellulosic biomass is usually less than 0.70, in particular 0.5 or less, more in particular 0.3 or less, or 0.2 or less. Herein the number of moles of carbohydrate is based on monosaccharide units, i.e. one mole of a oligo/polysaccharide having n monosaccharide units counts as n mol.

In absolute terms, the fermentable carbohydrate concentration is usually in the range of 65 to 400 g/L, in particular in the range of 100 to 250 g/L.

In absolute terms, the acetate concentration is usually in the range of 0.5 to 20 g/L, in particular in the range of 1-15 g/L, more in particular in the range of 2 to 12 g/L.

The pH can be chosen dependent on what is acceptable to the organism that is used, based on common general knowledge or can be routinely determined. Usually the fermentation is carried out at a neutral or acidic pH, in particular at a pH in the range of 2-7, more in particular at a pH of 3-6, even more in particular 3.5-5.5 (apparent pH as measured in the fermentation medium at the temperature at which fermentation takes place).

The temperature can be chosen dependent on what is acceptable to the organism that is used. Usually the temperature is in the range of 15-50 degrees C., in particular in the range of 25-45 degrees C.

As a fermentable carbohydrate in principle any carbohydrate can be used that is metabolised by the specific recombinant cell, with ethanol as a metabolic product. The cell may naturally comprise the required metabolic enzyme system or the cell may have been genetically modified to that purpose, e.g. as described by the review by Van Maris, the references cited therein, or as described in the present disclosure. Preferably, the fermentable carbohydrates in the hydrolysate comprise at least one carbohydrate selected from the group of hexoses, pentoses and oligosaccharides comprising one or more hexose and/or pentose units. In particular in case the recombinant cell is from the group Saccharomyces, preferably S. cerevisiae at least one carbohydrate selected from glucose, fructose, sucrose, maltose, galactose, xylose, arabinose and mannose is used. Good results have been obtained with glucose.

A method according to the invention is in particular suitable for preparing ethanol using a hydrolysate of at least one polymer selected from cellulose, hemicellulose and pectin, preferably at least one polymer selected from hemicellulose and pectin, because upon hydrolysis of these polymers acetate is typically released by hydrolysis or formed as a breakdown product. In particular, the hydrolysate may be hydrolysed lignocellulosic material, such as lignocellulosic biomass. For instance, lignocellulosic material may be selected from agricultural lignocellulosic material, for instance cotton, straw, (elephant) grass, bagasse, corn stover, lignocellulosic aquatic plant material, sugar beet pulp, citrus peels, lignocellulosic materials from forestry, such as lignocellulosic waste-materials from trees or bushes (trimmed/lopped/pruned plant material, saw dust, etc) or trees or bushes specifically grown as a source for lignocellulosic materials, e.g. poplar trees, (ligno)cellulosic waste from industry, e.g. wood-pulp, waste-paper.

Preferably, a lignocellulosic hydrolysate comprises one or more fermentable sugars (notably glucose, xylose and arabinose) and acetate, which have formed during hydrolysis. Thus, in a preferred embodiment of the invention the preparation of ethanol comprises a step wherein a lignocellulosic material is hydrolysed, thereby forming a hydrolysate comprising one or more fermentable carbohydrates, in particular glucose and optionally one or more other hexoses and pentoses, and acetate, which hydrolysate is thereafter contacted with a recombinant cell of the invention. The relative concentrations of acetate and fermentable carbohydrates in the substrate that is contacted with the recombinant cell of the invention can be modified by optimizing conditions for hydrolysis, by blending different hydrolysates and/or by blending with (partially) refined sources of carbohydrates and/or acetic acid.

Suitable hydrolysis methodology may be based on the Van Maris review cited above or the references cited therein, and include enzymatic hydrolysis, thermal hydrolysis, chemical hydrolysis and combinations thereof. The polymers are usually hydrolysed to the extent that at least 50%, preferably at least 90%, in particular at least 95% of the chains are degraded to monosaccharide units or to monosaccharide units and disaccharide units.

The invention is now illustrated by the following example:

EXAMPLES

Example 1

Materials and Methods

Strain Construction and Maintenance

The Saccharomyces cerevisiae strains used (Table 1) originate from the CEN.PK family, which was previously identified as a suitable background for combined genetic and physiological studies (van Dijken et al. (2000) Enzyme Microb. Technol. 26:706-714).

TABLE 1

Saccharomyces cerevisiae strains used

| Strain | Relevant genotype | Source/reference |
|---|---|---|
| CEN.PK113-5D | MATa ura3 GPD1 GPD2 | EUROSCARF strain collection, Frankfurt, Germany |
| IME076 (reference) | MATa ura3 GPD1 GPD2 p426_GPD(URA3) | |
| CEN.PK102-3A | MATa ura3 leu2 GPD1 GPD2 | EUROSCARF strain collection, Frankfurt, Germany |
| RWB0094 | MATa ura3 leu2 gpd1(−1,1133)::loxP-KanMX-loxP gpd2(−2,1281)::hphMX4 | BIRD Engineering, Rotterdam |
| IMZ008 | MATa ura3 leu2 gpd/(−1,1133)::loxP gpd2(−2,1281)::hphMX4 YEplac181(LEU2) | |
| IMZ 132 (CBS125049) | MATa ura3 leu2 gpd/(−1,1133)::loxP gpd2(−2,1281)::hphMX4 YEplac181(LEU2) pUDE43(URA3 pTHD3::mhpF (E. coli)::CYC1t) | Deposited at Centraalbureau voor Schimmelcultures on Jul. 16, 2009 |
| IMZ127 | MATa ura3 leu2 gpd/(−1,1133)::loxP gpd2Δ(−2,1281)::hphMX4 YEplac181(LEU2) p426_GPD(URA3) | |

To disrupt the GPD1 gene (YDL022W), the loxP-KanMX-loxP disruption cassette may be amplified by PCR according to Güldener et al. (1996, Nucleic Acids Res. 24:2519-2524), using a primer set containing 45-nucleotide flanking regions homologous to sequences within the GPD1 gene and approximately 20-nucleotide homologous to sequences of the disruption module of pUG6 (Güldener et al. (1996) Nucleic Acids Res. 24:2519-2524) (FIG. 2, Table 2). Similarly, plasmid pAG32 ((Goldstein and McCusker (1999) Yeast 15:1541-1553) may be used as a template for PCR amplification of the hphMX4 disruption module. For construction of a GPD2 (YOL059W) disruption cassette a primer set may be used containing 45-nucleotide flanking regions homologous to sequences within the GPD2 gene and 20-nucleic acid sequences homologous to sequences of the disruption module of pAG32 (Table 2).

TABLE 2

Oligonucleotides for inactivation of the GPD1 and GPD2 genes and for verification of correct disruption by diagnostic PCR. Gene disruption oligonucleotides; nucleotides homologous to the sequence to either the left (5' side) or right (3' side) of the genes to be deleted are indicated in capitals; lower case letters indicate nucleotides homologous to the sequence of the disruption cassettes.

| Target gene | GPD1/YDL022W | GPD2/YOL059W |
|---|---|---|
| Gene disruption primers | fw 5'TTGTACACCCCCCCCTCCACAAACACAAATATTGATAATATAAAcagctgaagcttcgtacgc [SEQ ID NO: 5] rv 5'AATCTAATCTTCATGTAGATCTAATTCTTGAATCATGTCCGGCGgcataggccactagtggatctg [SEQ ID NO: 6] | fw 5'TCAATTCTCTTTCCCTTTCCTTTTCCTTCGCTCCCCTTCCTTATCccaggctgaagcttcgtacg [SEQ ID NO: 7] rv 5'GTGTCTATTCGTCATGGATGCTAGCTCTTGAATCATCTCCGGTAGgcataggccactagtggatc [SEQ ID NO: 8] |
| Verification primers- target gene specific | fw 5'GPD1 5'CCCACCCACACCACCAATAC [SEQ ID NO: 9] rv 3'GPD1 5'CGGACGCCAGATGCTAGAAG [SEQ ID NO: 10] | fw 5'GPD2 5'GTTCAGCAGCTCTTCTCTAC [SEQ ID NO: 11] rv 3'GPD2 5'CCAAATGCGACATGAGTCAC [SEQ ID NO: 12] |
| Verification primers- disruption cassette specific | fw KANB 5'CGCACGTCAAGACTGTCAAG [SEQ ID NO: 13] rv KANA 5'TCGTATGTGAATGCTGGTCG [SEQ ID NO: 14] | Fw KANB 5'CGCACGTCAAGACTGTCAAG [SEQ ID NO: 15] rv KANA 5'TCGTATGTGAATGCTGGTCG [SEQ ID NO: 16] |

Transformation of the PCR amplified GPD1 and GPD2 disruption cassettes to *Saccharomyces cerevisiae* strain CEN.PK102-3A (Table 1) may be performed according to the protocols described by Güldener et al (Nucleic Acids Res. (1996) 24:2519-2524), followed by selection of transformants on YPD complex medium (Burke et al. (2000) Methods in yeast genetics. Cold Spring Harbour Press Plainview, N.Y.) with 200 mg/L G-418 for strains transformed with the KanMX disruption cassette and 300 mg/L hygromycin B for strains transformed with the hphMX4 disruption cassette. Confirmation of correct integration of the GPD1 gene disruption cassette may be checked by colony PCR, using combinations of primer sets 5' GPD1\KANA and 3'GPD1\KANB (Table 2). The correct inactivation of GPD2 can be similarly verified with primer sets 5' GPD2\KANA and 3'GPD2\KANB (Table 2). Strain RWB0094, carrying deletions in the open reading frames of the GPD1 and GPD2 genes of strain CEN.PK102-3A (MATa ura3 leu2) were replaced by the loxP-KanMX-loxP cassette and the hphMX4 cassette, respectively, was acquired from BIRD Engineering, Rotterdam, The Netherlands. The KanMX marker of strain RWB0094 was removed by expression of the Cre recombinase (Güldener et al (1996) Nucleic Acids Res. 24:2519-2524) and its leucine auxotrophy was complemented by transformation with the LEU2-bearing plasmid YEPlac181 (Gietz, R. D. and S. Akio. (1988) Gene 74:527-534.), yielding strain IMZ008. FIG. 1 2 schematically shows the gene disruption procedure, replacement of the GPD1 ORF by KanMX and GPD2 ORF by hphMX4. Arrows indicate oligonucleotide primers for verification by diagnostic PCR of correct gene inactivation.

Transformation of strain IMZ008 with the URA3-bearing mhpF expression plasmid pUDE43 (see below) yielded the prototrophic, mhpF-expressing strain IMZ132, transformation with the URA3-bearing 'empty' vector p426_GPD yielded strain IMZ127. Finally, transformation of strain CEN.PK113-5D (ura3) with p426_GPD yielded the prototrophic GPD1 GPD2 reference strain IME076. Cultures transformed with deletion cassettes were plated on YPD complex medium containing G418 (200 mg l$^{-1}$) or hygromycin (200 mg l$^{-1}$). Successful integration of the deletion cassettes was confirmed by diagnostic PCR.

Stock cultures of all strains were grown in shake flasks containing 100 ml of synthetic medium (see below) with 20 g l$^{-1}$ glucose as the carbon source. After adding 30% (v/v) glycerol, 1-ml aliquots of stationary phase cultures were stored at −80° C.

Plasmid Construction

The *E. coli* mhpF gene (EMBL accession number Y09555.7) was PCR amplified from *E. coli* K12 strain JM109 genomic DNA using primer pairs mhpF-FW (5'-GGGGACAAGTTTGTACAAAAAAGCAGGCTAT-GAGTAAGCGTAAAGTCGCCATTATCGG-3' [SEQ ID NO: 3]) and mhpF-RV (5'-GGGGACCACTTTGTA-CAAGAAAGCTGGGTGTTCATGCCGCTTCTCCTG-CCTTGC-3', [SEQ ID NO: 4]), which contained attB1 and attB2 sequences, respectively. The polymerase chain reaction (PCR) was performed using Phusion® Hot Start High-Fidelity DNA Polymerase (Finnzymes Oy, Espoo, Finland) according to manufacturer specifications and in a Biometra TGradient Thermocycler (Biometra, Gottingen, Germany) with the following settings: 25 cycles of 10 s denaturation at 98° C. and 30 s annealing and extension at 72° C. The 1011 bp PCR product was cloned using Gateway® cloning technology (Invitrogen, Carlsbad, Calif., USA). Plasmid pDONR221, using the BP reaction, was used to create the entry clone, designated as plasmid pUD64. From this entry clone and the multicopy plasmid pAG426GPD-ccdB (Addgene, Cambridge, Mass., USA) the yeast expression plasmid pUDE43, was constructed employing the LR reaction. Transformations of recombination reaction products into competent *E. coli* K12 strain JM109 were performed according to the Z-Competent™ *E. coli* Transformation Kit (Zymoresearch Corporation, Orange, USA) and plated on LB media containing either ampicillin (100 mg l$^{-1}$) or kanamycin (50 mg·l$^{-1}$). Yeast transformations were performed according to Burke et al. (Methods in yeast genetics (2000.) Cold Spring Harbor Laboratory Press Plainview, N.Y.) After transformations with the yeast expression plasmid, cells were plated on synthetic media. Successful insertion of multicopy plasmid pUDE43 was confirmed by diagnostic PCR using the primer pairs for cloning.

Cultivation and Media

Shake-flask cultivation was performed at 30° C. in a synthetic medium (46). The pH of the medium was adjusted to 6.0 with 2 M KOH prior to sterilization. Precultures were prepared by inoculating 100 ml medium containing 20 g l$^{-1}$ glucose in a 500 mL shake-flask with (1 ml) frozen stock culture. After 24 h incubation at 30° C. in an Innova® incubator shaker (200 rpm, New Brunswick Scientific, N.J., USA), cultures were transferred to bioreactors.

Anaerobic batch fermentations were carried out at 30° C. in 2-litre laboratory bioreactors (Applikon, Schiedam, The Netherlands) with a working volume of 1 litre. Synthetic medium with 20 g l$^{-1}$ glucose (46) was used for all fermentations and supplemented with 100 µl l$^{-1}$ of silicone antifoam (Silcolapse 5020, Caldic Belgium, Bleustar Silicones) as well as with the anaerobic growth factors, ergosterol (0.01 g l$^{-1}$) and Tween 80 (0.42 g l$^{-1}$) dissolved in ethanol. This resulted in 11-13 mM ethanol in the medium. Where indicated, acetic acid was added at a concentration of 2 g l$^{-1}$ and the pH was readjusted to 5.0 prior to inoculation. Culture pH was maintained at 5.0 by the automatic addition of 2M KOH. Cultures were stirred at 800 rpm and sparged with 0.5 L min$^{-1}$ nitrogen (<10 ppm oxygen). Dissolved oxygen was monitored with an autoclavable oxygen electrode (Applisens, Schiedam, The Netherlands). To minimize diffusion of oxygen, bioreactors were equipped with Norprene tubing (Cole Palmer Instrument Company, Vernon Hills, USA). All fermentations were carried out at least in duplicate.

Determination of Culture Dry Weight and Optical Density

Culture samples (10 ml) at selected time intervals were filtered over pre-weighed nitrocellulose filters (pore size 0.45 µm; Gelman Laboratory, Ann Arbor, USA). After removal of medium the filters were washed with demineralized water and dried in a microwave oven (Bosch, Stuttgart, Germany) for 20 min at 350 W and weighed. Duplicate determinations varied by less than 1%. Culture growth was also monitored via optical density readings at a wavelength of 660 nm on a Novaspec® II spectrophotometer.

Gas Analysis

Exhaust gas was cooled in a condensor (2° C.) and dried with a Permapure dryer type MD-110-48P-4 (Permapure, Toms River, USA). Oxygen and carbon dioxide concentrations were determined with a NGA 2000 analyzer (Rosemount Analytical, Orrville, USA). Exhaust gas-flow rate and carbon dioxide production rates were determined as described previously (3). In calculating these biomass-specific rates, a correction was made for volume changes caused by withdrawing culture samples.

Metabolite Analysis

Supernatant obtained by centrifugation of culture samples was analyzed for glucose, acetic acid, succinic acid, lactic acid, glycerol and ethanol via HPLC analysis on a Waters Alliance 2690 HPLC (Waters, Milford, USA) containing a Biorad HPX 87H column (Biorad, Hercules, USA). The column was eluted at 60° C. with 0.5 g l$^{-1}$H$_2$SO$_4$ at a flow rate of 0.6 ml min$^{-1}$. Detection was by means of a Waters 2410 refractive-index detector and a Waters 2487 UV detector. Initial and final glycerol concentrations were further determined using an enzymatic determination kit (R-Biopharm AG, Darmstadt, Germany). During cultivation in bioreactors that are sparged with nitrogen gas, a significant fraction of the ethanol is lost through the off gas. To correct for this, ethanol evaporation kinetics were analyzed in bioreactors operated under identical conditions at different working volumes with sterile synthetic medium. The resulting volume-dependent ethanol evaporation constants (for this set-up equal to 0.0080 divided by the volume in litres, expressed in h$^{-1}$) were used to correct HPLC measurements of ethanol concentrations in culture supernatants, taking into account changes in volume that were caused by sampling.

Enzyme Activity Assays

Cell extracts for activity assays of NAD$^+$-dependent acetaldehyde dehydrogenase (acetylating) were prepared from exponentially growing anaerobic batch cultures as described previously (Abbott et al., Appl. Environ. Microbiol. 75:2320-2325). NAD-dependent acetaldehyde dehydrogenase (acetylating) activity was measured at 30° C. by monitoring the oxidation of NADH at 340 nm. The reaction mixture (total volume 1 ml) contained 50 mM potassium phosphate buffer (pH 7.5), 15 mM NADH and cell extract. The reaction was started by addition of 0.5 mM acetyl-Coenzyme A. For glycerol 3-phosphate dehydrogenase (EC 1.1.1.8) activity determination, cell extracts were prepared as described above except that the phosphate buffer was replaced by triethanolamine buffer (10 mM, pH 5) (5,19). Glycerol-3-phosphate dehydrogenase activities were assayed in cell extracts at 30° C. as described previously (Blomberg and Adler (1989), J. Bacteriol. 171:1087-1092. Reaction rates were proportional to the amounts of cell extract added. Protein concentrations were determined by the Lowry method (Lowry et al (1951) J. Biol. Chem. 193:265-275) using bovine serum albumin as a standard.

Results

Growth and Product Formation in Anaerobic Batch Cultures

When cultures of the prototrophic reference strain S. cerevisiae IME076 (GPD1 GPD2) were supplemented with 2.0 g l$^{-1}$ acetic acid, the specific growth rate (0.32 h$^{-1}$) was identical to that reported for cultures grown in the absence of acetic acid (0.34 h$^{-1}$), Kuyper et al. (2005) FEMS Yeast Res. 5:399-409. The addition of acetic acid led to a slight decrease of the biomass yield and, consequently a decrease of the glycerol yield on glucose relative to cultures grown in the absence of acetic acid (FIG. 2, Table 3).

This effect has been attributed to the higher rate of glucose dissimilation for intracellular pH homeostasis due to diffusion of acetic acid into the cell, which in turn results in a lower biomass yield on glucose. Under the same conditions, an isogenic gpd1Δgpd2Δ strain, in which absence of NAD$^+$-dependent glycerol-3-phosphate dehydrogenase activity was confirmed in cell extracts (Table 2), was completely unable to grow anaerobically (FIG. 2), consistent with the notion that glycerol production via Gpd1 and Gpd2 is essential for NADH reoxidation in anaerobic cultures of S. cerevisiae.

TABLE 3

Physiology of the engineered S. cerevisiae strain IMZ132 and the empty-vector reference strain IME076 during anaerobic batch cultivation on synthetic medium (pH 5) with glucose-acetate mixtures

| Yeast strain | IME076 | IMZ132 |
| --- | --- | --- |
| Relevant genotype | GPD1 GPD2 | gpd1Δ gpd2Δ + mhpF |
| Glycerol 3-phosphate dehydrogenase (µmol mg protein$^{-1}$ min$^{-1}$) | 0.034 ± 0.003 | <0.002 |
| Acetaldehyde dehydrogenase (acetylating) (µmol mg protein$^{-1}$ min$^{-1}$) | <0.002 | 0.020 ± 0.004 |
| Specific growth rate (h$^{-1}$) | 0.32 ± 0.01 | 0.14 ± 0.01 |
| Biomass yield on glucose (g g$^{-1}$) | 0.083 ± 0.000 | 0.082 ± 0.009 |
| Biomass yield on acetate (g g$^{-1}$) | n.a. | 3.8 ± 0.5 |
| Glycerol yield on glucose (g g$^{-1}$) | 0.073 ± 0.007 | <0.002 |
| Ethanol yield on glucose (g g$^{-1}$) Not corrected for evaporation | 0.39 ± 0.01 | 0.43 ± 0.01 |
| Ethanol yield on glucose (g g$^{-1}$) Corrected for evaporation | 0.41 ± 0.01 | 0.47 ± 0.01 | n.a., not applicable.

Expression of the E. coli mhpF gene in a gpd1Δgpd2Δ strain, resulting in acetyl-CoA dependent rates of NADH reduction in cell extracts of 0.020 μmol min$^{-1}$ (mg protein)$^{-1}$ (Table 3), did not enable anaerobic growth when glucose was the sole carbon source. However, when the medium was supplemented with 2.0 g l$^{-1}$ acetic acid, exponential growth was observed at a specific growth rate of 0.14 h$^{-1}$. No formation of glycerol occurred during cultivation. (FIG. 2, Table 3). The trace amounts (<1 mM) of glycerol present in cultures of gpd1Δgpd2Δ strains originate from the inoculum cultures which were started from frozen glycerol stocks. Ethanol was the major organic product and the small amounts of succinate and lactate produced were similar to those observed in cultures of the reference strain grown under the same conditions (data not shown).

It is observed that the IMZ132 fermentations (40 h) lasted longer than the wild type strain (15 h) and the anaerobic batch cultures were sparged with nitrogen gas. Accordingly, the fraction of ethanol lost through evaporation was higher for strain IMZ132. After determination of the kinetics of ethanol evaporation in sterile control experiments and correction of the ethanol yields, a 13% higher apparent ethanol yield on glucose was shown for the engineered strain according to the invention, using the linear pathway for NADH dependent reduction of acetic acid to ethanol (Table 3).

Discussion

The present study provides a proof of principle that, stoichiometrically, the role of glycerol as a redox sink for anaerobic growth of S. cerevisiae can be fully replaced by a linear pathway for NADH-dependent reduction of acetate to ethanol. This offers interesting perspectives for large-scale ethanol production from feedstocks that contain acetic acid, such as lignocellulosic hydrolysates.

In addition to reducing the organic carbon content of spent media and increasing the ethanol yield, the reduction of acetic acid to ethanol may at least partially alleviate acetate inhibition of yeast growth and metabolism, which is especially problematic at low pH and during the consumption of pentose sugars by engineered yeast strains Example 2

This example relates to the fermentative glycerol-free ethanol production by a gpd1Δgpd2Δ Saccharomyces. cerevisiae strain expressing a codon optimised version (SEQ ID NO: 28) of the wild type dmpF gene from Pseudomonas sp. CF600 (GenBank No: CAA43226) (Shingler et al. (1992) J. Bacteriol. 174:71 1-24).

For this purpose, the same procedures and techniques used for the construction and evaluation of the performance of the strain IMZ132 (gpd1Δgpd2Δ mhpF) were used. These procedures and techniques are described in Materials and Methods section of Example 1. In this work, transformation of strain IMZ008 (gpd1Δgpd2Δura3d) with the URA3-bearing dmpF expression plasmid pUDE47 yielded the prototrophic, dmpF-expressing strain IMZ130. For the construction of plasmid pUDE47, a codon optimized copy of the dmpF gene (EMBL accession number X60835.1) from Pseudomonas sp. CF600 was ligated into p426_GPD plasmid. Codon optimization for the expression in S. cerevisiae and ligation into the plasmid p426_GPD were performed by BaseClear BV (Leiden, The Netherlands). Successful insertion of multicopy plasmid pUDE47 was confirmed using diagnostic colony PCR using the primer pairs dmpF-FW (CATTGATTGCGCCATACG (SEQ ID NO:30)) and dmpF-RV (CCGGTAATATCGGAACAGAC (SEQ ID NO:31).

Results

Growth and Product Formation in Anaerobic Batch Cultures

Expression of the Pseudomonas sp. CF600 dmpF gene in a gpd1Δgpd2Δ S. cerevisiae strain gave similar results to the obtained for the expression of E. coli mhpF gene in the same strain. In anaerobic batch fermentations, similar to strain IMZ132 (gpd1Δ gpd2Δ mhpF), functional expression of dmpF gene together with supplementation of the medium with 2.0 g l$^{-1}$ acetic acid, resulted in exponential growth with a specific growth rate of 0.11 h$^{-1}$ (FIG. 1). Strain IMZ130 (gpd1Δgpd2Δ dmpF) had a slightly longer batch time (55 h) than strain IMZ132 (40 h). During cultivation, initial concentration of 20 g l$^{-1}$ of glucose was completely consumed, while no glycerol formation was observed. At the same time, acetate was consumed from 2.1 g l$^{-1}$ initial concentration to 1.6 g l$^{-1}$ final concentration. Ethanol was the major organic product, exhibiting an ethanol yield on glucose of 0.48 g g$^{-1}$ (yield corrected by ethanol evaporation). Small amounts of succinate and lactate were produced, similar to those observed in cultures of the reference strain grown under the same conditions.

Figure 3:
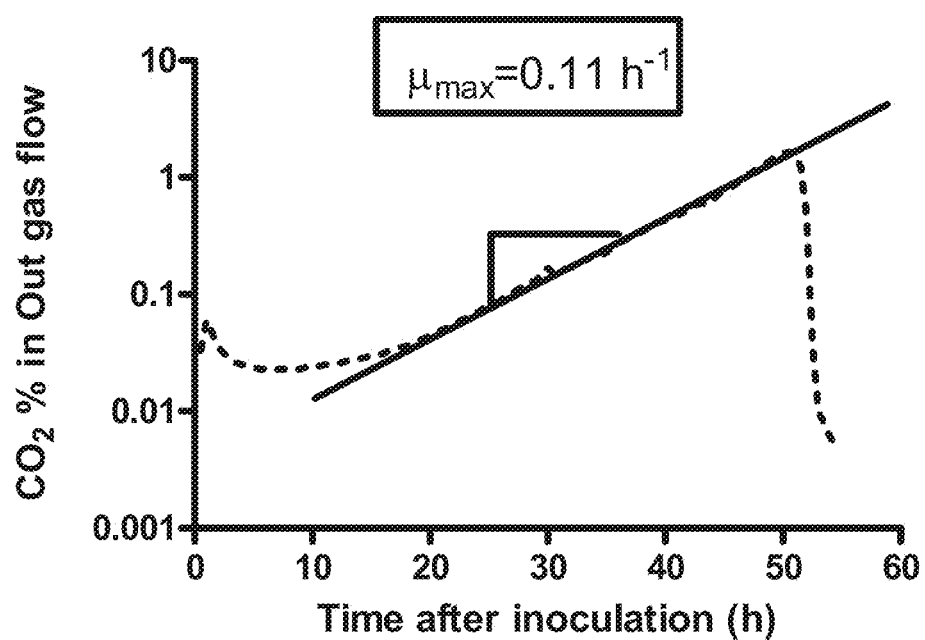
FIG. 3 shows the volumetric $CO_2$ percentage present in the out flow of a batch fermentation inoculated with strain IMZ130 (gpd1Δgpd2ΔmpF). The graph is presented in a logarithmic scale on the y-axis in order to demonstrate exponential growth and calculate the maximum specific growth rate.

FIG. 3 shows the volumetric $CO_2$ percentage present in the out flow of a batch fermentation inoculated with strain IMZ130 (gpd1Δgpd2Δ dmpF). The graph is presented in a logarithmic scale on the y-axis in order to demonstrate exponential growth and calculate the maximum specific growth rate.

The insertion of a synthetic codon optimized copy of the gene dmpF from Pseudomonas sp. CF600, provides another example that it is stoichiometrically possible to substitute glycerol formation as a redox sink in anaerobic growth of S. cerevisiae by a linear metabolic pathway for NADH-dependent reduction of acetate to ethanol. Also this example shows that the insertion of (acetalyting) acetaldehyde dehydrogenase in a gpd1Δgpd2Δ S. cerevisiae strain resulted in higher ethanol yields on glucose, no formation of by-product glycerol, and the consumption of fermentation inhibitor compound acetate.

```
Sequences
SEQ ID NO: 1
E. coli mhpF gene Acetaldehyde
dehydrogenase, acylating
ATGAGTAAGCGTAAAGTCGCCATTATCGGTTCTGGCAACATTGGT

ACCGATCTGATGATTAAAATTTTGCGTCACGGTCAGCATCTGGAG

ATGGCGGTGATGGTTGGCATTGATCCTCAGTCCGACGGTCTGGCG

CGCGCCAGACGTATGGGCGTCGCCACCACCCATGAAGGGGTGATC

GGACTGATGAACATGCCTGAATTTGCTGATATCGACATTGTATTT

GATGCGACCAGCGCCGGTGCTCATGTGAAAAACGATGCCGCTTTA

CGCGAAGCGAAACCGGATATTCGCTTAATTGACCTGACGCCTGCT

GCCATCGGCCCTTACTGCGTGCCGGTGGTTAACCTCGAGGCGAAC

GTCGATCAACTGAACGTCAACATGGTCACCTGCGGCGGCCAGGCC

ACCATTCCAATGGTGGCGGCAGTTTCACGCGTGGCGCGTGTTCAT

TACGCCGAAATTATCGCTTCTATCGCCAGTAAATCTGCCGGACCT

GGCACGCGTGCCAATATCGATGAATTTACGGAAACCACTTCCCGA

GCCATTGAAGTGGTGGGCGGCGCGGCAAAAGGGAAGGCGATTATT

GTGCTTAACCCAGCAGAGCCACCGTTGATGATGCGTGACACGGTG
```

```
TATGTATTGAGCGACGAAGCTTCACAAGATGATATCGAAGCCTCA

ATCAATGAAATGGCTGAGGCGGTGCAGGCTTACGTACCGGGTTAT

CGCCTGAAACAGCGCGTGCAGTTTGAAGTTATCCCGCAGGATAAA

CCGGTCAATTTACCGGGCGTGGGGCAATTCTCCGGACTGAAAACA

GCGGTCTGGCTGGAAGTCGAAGGCGCAGCGCATTATCTGCCTGCC

TATGCGGGCAACCTCGACATTATGACTTCCAGTGCGCTGGCGACA

GCGGAAAAAATGGCCCAGTCACTGGCGCGCAAGGCAGGAGAAGCG

GCATGA

SEQ ID NO: 2
E. coli Acetaldehyde dehydrogenase
OS = Escherichia coli (strain K12)
GN = mhpF PE = 1 SV = 1
MSKRKVAIIGSGNIGTDLMIKILRHGQHLEMAVMVGIDPQSDGLA

RARRMGVATTHEGVIGLMNMPEFADIDIVFDATSAGAHVKNDAAL

REAKPDIRLIDLTPAAIGPYCVPVVNLEANVDQLNVNMVTCGGQA

TIPMVAAVSRVARVHYAEIIASIASKSAGPGTRANIDEFTETTSR

AIEVVGGAAKGKAIIVLNPAEPPLMMRDTVYVLSDEASQDDIEAS

INEMAEAVQAYVPGYRLKQRVQFEVIPQDKPVNLPGVGQFSGLKT

AVVVLEVEGAAHYLPAYAGNLDIMTSSALATAEKMAQSLARKAGE

AA

SEQ ID NO: 3
primer mhpF-FW
GGGGACAAGTTTGTACAAAAAAGCAGGCTATGAGTAAGCGTAAAG

TCGCCATTATCGG

SEQ ID NO: 4
primer mhpF-RV
GGGGACCACTTTGTACAAGAAAGCTGGGTGTTCATGCCGCTTCTC

CTGCCTTGC

SEQ ID NO: 5
GPD1/YDL022W fw gene disruption primer
TTGTACACCCCCCCCTCCACAACACAAATATTGATAATATAAA cagctgaagcttcgtacgc SEQ ID NO: 6
GPD1/YDL022W rv gene disruption primer
AATCTAATCTTCATGTAGATCTAATTCTTCAATCATGTCCGGCGg cataggccactagtggatctg SEQ ID NO: 7
GPD2/YOL059W fw gene disruption
primer
TCAATTCTCTTTCCCTTTCCTTTTCCTTCGCTCCCCTTCCTTAT Cccaggctgaagcttcgtacg SEQ ID NO: 8
GPD2/YOL059W rv gene disruption
primer
GTGTCTATTCGTCATCGATGTCTAGCTCTTCAATCATCTCCGGTA Ggcataggccactagtggatc SEQ ID NO: 9
GPD1/YDL022W fw verification primer
CCCACCCACACCACCAATAC SEQ ID NO: 10
GPD1/YDL022W rv verification primer
CGGACGCCAGATGCTAGAAG SEQ ID NO: 11
GPD2/YOL059W fw verification primer
GTTCAGCAGCTCTTCTCTAC SEQ ID NO: 12
GPD2/YOL059W rv verification primer
CCAAATGCGACATGAGTCAC SEQ ID NO: 13
GPD1/YDL022W fw disruption cassette
specific verification primer
CGCACGTCAAGACTGTCAAG SEQ ID NO: 14
GPD1IYDL022W rv disruption cassette
specific verification primer
TCGTATGTGAATGCTGGTCG SEQ ID NO: 15
GPD2/YOL059W fw disruption cassette
specific verification primer
CGCACGTCAAGACTGTCAAG SEQ ID NO: 16
GPD2/YOL059W rv disruption cassette
specific verification primer
TCGTATGTGAATGCTGGTCG SEQ ID NO: 17
S. cerevisiae ACS 1 gene
ATGTCGCCCTCTGCCGTACAATCATCAAAACTAGAAGAACAGTCAAGTG

AAATTGACAAGTTGAAAGCAAAAATGTCCCAGTCTGCCGCCACTGCGCA

GCAGAAGAAGGAACATGAGTATGAACATTTGACTTCGGTCAAGATCGTG

CCACAACGGCCCATCTCAGATAGACTGCAGCCCGCAATTGCTACCCACT

ATTCTCCACACTTGGACGGGTTGCAGGACTATCAGCGCTTGCACAAGGA

GTCTATTGAAGACCCTGCTAAGTTCTTCGGTTCTAAAGCTACCCAATTT

TTAAACTGGTCTAAGCCATTCGATAAGGTGTTCATCCCAGACCCTAAAA

CGGGCAGGCCCTCCTTCCAGAACAATGCATGGTTCCTCAACGGCCAATT

AAACGCCTGTTACAACTGTGTTGACAGACATGCCTTGAAGACTCCTAAC

AAGAAAGCCATTATTTTCGAAGGTGACGAGCCTGGCCAAGGCTATTCCA

TTACCTACAAGGAACTACTTGAAGAAGTTTGTCAAGTGGCACAAGTGCT

GACTTACTCTATGGGCGTTCGCAAGGGCGATACTGTTGCCGTGTACATG

CCTATGGTCCCAGAAGCAATCATAACCTTGTTGGCCATTTCCCGTATCG

GTGCCATTCACTCCGTAGTCTTTGCCGGGTTTTCTTCCAACTCCTTGAG

AGATCGTATCAACGATGGGGACTCTAAAGTTGTCATCACTACAGATGAA

TCCAACAGAGGTGGTAAAGTCATTGAGACTAAAAGAATTGTTGATGACG

CGCTAAGAGAGACCCCAGGCGTGAGACACGTCTTGGTTTATAGAAAGAC

CAACAATCCATCTGTTGCTTTCCATGCCCCCAGAGATTTGGATTGGGCA

ACAGAAAGAAGAAATACAAGACCTACTATCCATGCACACCCGTTGATT

CTGAGGATCCATTATTCTTGTTGTATACGTCTGGTTCTACTGGTGCCCC

CAAGGGTGTTCAACATTCTACCGCAGGTTACTTGCTGGGAGCTTTGTTG

ACCATGCGCTACACTTTTGACACTCACCAAGAAGACGTTTTCTTCACAG

CTGGAGACATTGGCTGGATTACAGGCCACACTTATGTGGTTTATGGTCC

CTTACTATATGGTTGTGCCACTTTGGTCTTTGAAGGGACTCCTGCGTAC

CCAAATTACTCCCGTTATTGGGATATTATTGATGAACACAAAGTCACCC
```

```
AATTTTATGTTGCGCCAACTGCTTTGCGTTTGTTGAAAAGAGCTGGTGA
TTCCTACATCGAAAATCATTCCTTAAAATCTTTGCGTTGCTTGGGTTCG
GTCGGTGAGCCAATTGCTGCTGAAGTTTGGGAGTGGTACTCTGAAAAAA
TAGGTAAAAATGAAATCCCCATTGTAGACACCTACTGGCAAACAGAATC
TGGTTCGCATCTGGTCACCCCGCTGGCTGGTGGTGTTACACCAATGAAA
CCGGGTTCTGCCTCATTCCCCTTCTTCGGTATTGATGCAGTTGTTCTTG
ACCCTAACACTGGTGAAGAACTTAACACCAGCCACGCAGAGGGTGTCCT
TGCCGTCAAAGCTGCATGGCCATCATTTGCAAGAACTATTTGGAAAAAT
CATGATAGGTATCTAGACACTTATTTGAACCCTTACCCTGGCTACTATT
TCACTGGTGATGGTGCTGCAAAGGATAAGGATGGTTATATCTGGATTTT
GGGTCGTGTAGACGATGTGGTGAACGTCTCTGGTCACCGTCTGTCTACC
GCTGAAATTGAGGCTGCTATTATCGAAGATCCAATTGTGGCCGAGTGTG
CTGTTGTCGGATTCAACGATGACTTGACTGGTCAAGCAGTTGCTGCATT
TGTGGTGTTGAAAAACAAATCTAGTTGGTCCACCGCAACAGATGATGAA
TTACAAGATATCAAGAAGCATTTGGTCTTTACTGTTAGAAAAGACATCG
GGCCATTTGCCGCACCAAAATTGATCATTTTAGTGGATGACTTGCCCAA
GACAAGATCCGGCAAAATTATGAGACGTATTTTAAGAAAAATCCTAGCA
GGAGAAAGTGACCAACTAGGCGACGTTTCTACATTGTCAAACCCTGGCA
TTGTTAGACATCTAATTGATTCGGTCAAGTTGTAA

SEQ ID NO: 18
S. cerevisiae ACS 2 gene
ATGACAATCAAGGAACATAAAGTAGTTTATGAAGCTCACAACGTAAAGG
CTCTTAAGGCTCCTCAACATTTTTACAACAGCCAACCCGGCAAGGGTTA
CGTTACTGATATGCAACATTATCAAGAAATGTATCAACAATCTATCAAT
GAGCCAGAAAAATTCTTTGATAAGATGGCTAAGGAATACTTGCATTGGG
ATGCTCCATACACCAAAGTTCAATCTGGTTCATTGAACAATGGTGATGT
TGCATGGTTTTTGAACGGTAAATTGAATGCATCATACAATTGTGTTGAC
AGACATGCCTTTGCTAATCCCGACAAGCCAGCTTTGATCTATGAAGCTG
ATGACGAATCCGACAACAAAATCATCACATTTGGTGAATTACTCAGAAA
AGTTTCCCAAATCGCTGGTGTCTTAAAAAGCTGGGGCGTTAAGAAAGGT
GACACAGTGGCTATCTATTTGCCAATGATTCCAGAAGCGGTCATTGCTA
TGTTGGCTGTGGCTCGTATTGGTGCTATTCACTCTGTTGTCTTTGCTGG
GTTCTCCGCTGGTTCGTTGAAAGATCGTGTCGTTGACGCTAATTCTAAA
GTGGTCATCACTTGTGATGAAGGTAAAAGAGGTGGTAAGACCATCAACA
CTAAAAAAATTGTTGACGAAGGTTTGAACGGAGTCGATTTGGTTTCCCG
TATCTTGGTTTTCCAAAGAACTGGTACTGAAGGTATTCCAATGAAGGCC
GGTAGAGATTACTGGTGGCATGAGGAGGCCGCTAAGCAGAGAACTTACC
TACCTCCTGTTTCATGTGACGCTGAAGATCCTCTATTTTTATTATACAC
TTCCGGTTCCACTGGTTCTCCAAAGGGTGTCGTTCACACTACAGGTGGT
TATTTATTAGGTGCCGCTTTAACAACTAGATACGTTTTTGATATTCACC
CAGAAGATGTTCTCTTCACTGCCGGTGACGTCGGCTGGATCACGGGTCA
CACCTATGCTCTATATGGTCCATTAACCTTGGGTACCGCCTCAATAATT TTCGAATCCACTCCTGCCTACCCAGATTATGGTAGATATTGGAGAATTA
TCCAACGTCACAAGGCTACCCATTTCTATGTGGCTCCAACTGCTTTAAG
ATTAATCAAACGTGTAGGTGAAGCCGAAATTGCCAAATATGACACTTCC
TCATTACGTGTCTTGGGTTCCGTCGGTGAACCAATCTCTCCAGACTTAT
GGGAATGGTATCATGAAAAGTGGGTAACAAAAACTGTGTCATTTGTGA
CACTATGTGGCAAACAGAGTCTGGTTCTCATTTAATTGCTCCTTTGGCA
GGTGCTGTCCCAACAAAACCTGGTTCTGCTACCGTGCCATTCTTTGGTA
TTAACGCTTGTATCATTGACCCTGTTACAGGTGTGGAATTAGAAGGTAA
TGATGTCGAAGGTGTCCTTGCCGTTAAATCACCATGGCCATCAATGGCT
AGATCTGTTTGGAACCACCACGACCGTTACATGGATACTTACTTGAAAC
CTTATCCTGGTCACTATTTCACAGGTGATGGTGCTGGTAGAGATCATGA
TGGTTACTACTGGATCAGGGGTAGAGTTGACGACGTTGTAAATGTTTCC
GGTCATAGATTATCCACATCAGAAATTGAAGCATCTATCTCAAATCACG
AAAACGTCTCGGAAGCTGCTGTTGTCGGTATTCCAGATGAATTGACCGG
TCAAACCGTCGTTGCATATGTTTCCCTAAAAGATGGTTATCTACAAAAC
AACGCTACTGAAGGTGATGCAGAACACATCACACCAGATAATTTACGTA
GAGAATTGATCTTACAAGTTAGGGGTGAGATTGGTCCTTTCGCCTCACC
AAAAACCATTATTCTAGTTAGAGATCTACCAAGAACAAGGTCAGGAAAG
ATTATGAGAAGAGTTCTAAGAAAGGTTGCTTCTAACGAAGCCGAACAGC
TAGGTGACCTAACTACTTTGGCCAACCCAGAAGTTGTACCTGCCATCAT
TTCTGCTGTAGAGAACCAATTTTTCTCTCAAAAAAAGAAATAA SEQ ID NO: 19
S. cerevisiae ADH1
ATGTCTATCCCAGAAACTCAAAAAGGTGTTATCTTCTACGAATCCCACG
GTAAGTTGGAATACAAAGATATTCCAGTTCCAAAGCCAAAGGCCAACGA
ATTGTTGATCAACGTTAAATACTCTGGTGTCTGTCACACTGACTTGCAC
GCTTGGCACGGTGACTGGCCATTGCCAGTTAAGCTACCATTAGTCGGTG
GTCACGAAGGTGCCGGTGTCGTTGTCGGCATGGGTGAAAACGTTAAGGG
CTGGAAGATCGGTGACTACGCCGGTATCAAATGGTTGAACGGTTCTTGT
ATGGCCTGTGAATACTGTGAATTGGGTAACGAATCCAACTGTCCTCACG
CTGACTTGTCTGGTTACACCCACGACGGTTCTTTCCAACAATACGCTAC
CGCTGACGCTGTTCAAGCCGCTCACATTCCTCAAGGTACCGACTTGGCC
CAAGTCGCCCCCATCTTGTGTGCTGGTATCACCGTCTACAAGGCTTTGA
AGTCTGCTAACTTGATGGCCGGTCACTGGGTTGCTATCTCCGGTGCTGC
TGGTGGTCTAGGTTCTTTGGCTGTTCAATACGCCAAGGCTATGGGTTAC
AGAGTCTTGGGTATTGACGGTGGTGAAGGTAAGGAAGAATTATTCAGAT
CCATCGGTGGTGAAGTCTTCATTGACTTCACTAAGGAAAAGGACATTGT
CGGTGCTGTTCTAAAGGCCACTGACGGTGGTGCTCACGGTGTCATCAAC
GTTTCCGTTTCCGAAGCCGCTATTGAAGCTTCTACCAGATACGTTAGAG
CTAACGGTACCACCGTTTTGGTCGGTATGCCAGCTGGTGCCAAGTGTTG
TTCTGATGTCTTCAACCAAGTCGTCAAGTCCATCTCTATTGTTGGTTCT
```

-continued
```
TACGTCGGTAACAGAGCTGACACCAGAGAAGCTTTGGACTTCTTCGCCA
GAGGTTTGGTCAAGTCTCCAATCAAGGTTGTCGGCTTGTCTACCTTGCC
AGAAATTTACGAAAAGATGGAAAAGGGTCAAATCGTTGGTAGATACGTT
GTTGACACTTCTAAATAA SEQ ID NO: 20
S. cerevisiae ADH2
ATGTCTATTCCAGAAACTCAAAAAGCCATTATCTTCTACGAATCCAACG
GCAAGTTGGAGCATAAGGATATCCCAGTTCCAAAGCCAAAGCCCAACGA
ATTGTTAATCAACGTCAAGTACTCTGGTGTCTGCCACACCGATTTGCAC
GCTTGGCATGGTGACTGGCCATTGCCAACTAAGTTACCATTAGTTGGTG
GTCACGAAGGTGCCGGTGTCGTTGTCGGCATGGGTGAAAACGTTAAGGG
CTGGAAGATCGGTGACTACGCCGGTATCAAATGGTTGAACGGTTCTTGT
ATGGCCTGTGAATACTGTGAATTGGGTAACGAATCCAACTGTCCTCACG
CTGACTTGTCTGGTTACACCCACGACGGTTCTTTCCAAGAATACGCTAC
CGCTGACGCTGTTCAAGCCGCTCACATTCCTCAAGGTACTGACTTGGCT
GAAGTCGCGCCAATCTTGTGTGCTGGTATCACCGTATACAAGGCTTTGA
AGTCTGCCAACTTGAGAGCAGGCCACTGGGCGGCCATTTCTGGTGCTGC
TGGTGGTCTAGGTTCTTTGGCTGTTCAATATGCTAAGGCGATGGGTTAC
AGAGTCTTAGGTATTGATGGTGGTCCAGGAAAGGAAGAATTGTTTACCT
CGCTCGGTGGTGAAGTATTCATCGACTTCACCAAAGAGAAGGACATTGT
TAGCGCAGTCGTTAAGGCTACCAACGGCGGTGCCCACGGTATCATCAAT
GTTTCCGTTTCCGAAGCCGCTATCGAAGCTTCTACCAGATACTGTAGGG
CGAACGGTACTGTTGTCTTGGTTGGTTTGCCAGCCGGTGCAAAGTGCTC
CTCTGATGTCTTCAACCACGTTGTCAAGTCTATCTCCATTGTCGGCTCT
TACGTGGGGAACAGAGCTGATACCAGAGAAGCCTTAGATTTCTTTGCCA
GAGGTCTAGTCAAGTCTCCAATAAAGGTAGTTGGCTTATCCAGTTTACC
AGAAATTTACGAAAAGATGGAGAAGGGCCAAATTGCTGGTAGATACGTT
GTTGACACTTCTAAATAA SEQ ID NO: 21
S. cerevisiae ADH3
ATGTTGAGAACGTCAACATTGTTCACCAGGCGTGTCCAACCAAGCCTAT
TTTCTAGAAACATTCTTAGATTGCAATCCACAGCTGCAATCCCTAAGAC
TCAAAAGGTGTCATCTTTTATGAGAATAAGGGGAAGCTGCATTACAAA
GATATCCCTGTCCCCGAGCCTAAGCCAAATGAAATTTTAATCAACGTTA
AATATTCTGGTGTATGTCACACCGATTTACATGCTTGGCACGGCGATTG
GCCATTACCTGTTAAACTACCATTAGTAGGTGGTCATGAAGGTGCTGGT
GTAGTTGTCAAACTAGGTTCCAATGTCAAGGGCTGGAAAGTCGGTGATT
TAGCAGGTATCAAATGGCTGAACGGTTCTTGTATGACATGCGAATTCTG
TGAATCAGGTCATGAATCAAATTGTCCAGATGCTGATTTATCTGGTTAC
ACTCATGATGGTTCTTTCCAACAATTTGCGACCGCTGATGCTATTCAAG
CCGCCAAAATTCAACAGGGTACCGACTTGGCCGAAGTAGCCCCAATATT
ATGTGCTGGTGTTACTGTATATAAAGCACTAAAAGAGGCAGACTTGAAA
GCTGGTGACTGGGTTGCCATCTCTGGTGCTGCAGGTGGCTTGGGTTCCT
```

```
TGGCCGTTCAATATGCAACTGCGATGGGTTACAGAGTTCTAGGTATTGA
TGCAGGTGAGGAAAAGGAAAAACTTTTCAAGAAATTGGGGGGTGAAGTA
TTCATCGACTTTACTAAAACAAAGAATATGGTTTCTGACATTCAAGAAG
CTACCAAAGGTGGCCCTCATGGTGTCATTAACGTTTCCGTTTCTGAAGC
CGCTATTTCTCTATCTACGGAATATGTTAGACCATGTGGTACCGTCGTT
TTGGTTGGTTTGCCCGCTAACGCCTACGTTAAATCAGAGGTATTCTCTC
ATGTGGTGAAGTCCATCAATATCAAGGGTTCTTATGTTGGTAACAGAGC
TGATACGAGAGAAGCCTTAGACTTCTTTAGCAGAGGTTTGATCAAATCA
CCAATCAAAATTGTTGGATTATCTGAATTACCAAAGGTTTATGACTTGA
TGGAAAAGGGCAAGATTTTGGGTAGATACGTCGTCGATACTAGTAAATA
A

SEQ ID NO: 22
S. cerevisiae ADH4
ATGTCTTCCGTTACTGGGTTTTACATTCCACCAATCTCTTTCTTTGGTG
AAGGTGCTTTAGAAGAAACCGCTGATTACATCAAAAACAAGGATTACAA
AAAGGCTTTGATCGTTACTGATCCTGGTATTGCAGCTATTGGTCTCTCC
GGTAGAGTCCAAAAGATGTTGGAAGAACGTGACTTAAACGTTGCTATCT
ATGACAAAACTCAACCAAACCCAAATATTGCCAATGTCACAGCTGGTTT
GAAGGTTTTGAAGGAACAAAACTCTGAAATTGTTGTTTCCATTGGTGGT
GGTTCTGCTCACGACAATGCTAAGGCCATTGCTTTATTGGCTACTAACG
GTGGGGAAATCGGAGACTATGAAGGTGTCAATCAATCTAAGAAGGCTGC
TTTACCACTATTTGCCATCAACACTACTGCTGGTACTGCTTCCGAAATG
ACCAGATTCACTATTATCTCTAATGAAGAAAGAAAATCAAGATGGCTA
TCATTGACAACAACGTCACTCCAGCTGTTGCTGTCAACGATCCATCTAC
CATGTTTGGTTTGCCACCTGCTTTGACTGCTGCTACTGGTCTAGATGCT
TTGACTCACTGTATCGAAGCTTATGTTTCCACCGCCTCTAACCCAATCA
CCGATGCCTGTGCTTTGAAGGGTATTGATTTGATCAATGAAAGCTTAGT
CGCTGCATACAAAGACGGTAAAGACAAGAAGGCCAGAACTGACATGTGT
TACGCTGAATACTTGGCAGGTATGGCTTTCAACAATGCTTCTCTAGGTT
ATGTTCATGCCCTTGCTCATCAACTTGGTGGTTTCTACCACTTGCCTCA
TGGTGTTTGTAACGCTGTCTTGTTGCCTCATGTTCAAGAGGCCAACATG
CAATGTCCAAAGGCCAAGAAGAGATTAGGTGAAATTGCTTTGCATTTCG
GTGCTTCTCAAGAAGATCCAGAAGAAACCATCAAGGCTTTGCACGTTTT
AAACAGAACCATGAACATTCCAAGAAACTTGAAAGAATTAGGTGTTAAA
ACCGAAGATTTTGAAATTTTGGCTGAACACGCCATGCATGATGCCTGCC
ATTTGACTAACCCAGTTCAATTCACCAAAGAACAAGTGGTTGCCATTAT
CAAGAAAGCCTATGAATATTAA SEQ ID NO: 23
S. cerevisiae ADH5
ATGCCTTCGCAAGTCATTCCTGAAAAACAAAAGGCTATTGTCTTTTATG
AGACAGATGGAAAATTGGAATATAAAGACGTCACAGTTCCGGAACCTAA
GCCTAACGAAATTTTAGTCCACGTTAAATATTCTGGTGTTTGTCATAGT
```

```
GACTTGCACGCGTGGCACGGTGATTGGCCATTTCAATTGAAATTTCCAT
TAATCGGTGGTCACGAAGGTGCTGGTGTTGTTGTTAAGTTGGGATCTAA
CGTTAAGGGCTGGAAAGTCGGTGATTTTGCAGGTATAAAATGGTTGAAT
GGGACTTGCATGTCCTGTGAATATTGTGAAGTAGGTAATGAATCTCAAT
GTCCTTATTTGGATGGTACTGGCTTCACACATGATGGTACTTTTCAAGA
ATACGCAACTGCCGATGCCGTTCAAGCTGCCCATATTCCACCAAACGTC
AATCTTGCTGAAGTTGCCCCAATCTTGTGTGCAGGTATCACTGTTTATA
AGGCGTTGAAAAGAGCCAATGTGATACCAGGCCAATGGGTCACTATATC
CGGTGCATGCGGTGGCTTGGGTTCTCTGGCAATCCAATACGCCCTTGCT
ATGGGTTACAGGGTCATTGGTATCGATGGTGGTAATGCCAAGCGAAAGT
TATTTGAACAATTAGGCGGAGAAATATTCATCGATTTCACGGAAGAAAA
AGACATTGTTGGTGCTATAATAAAGGCCACTAATGGCGGTTCTCATGGA
GTTATTAATGTGTCTGTTTCTGAAGCAGCTATCGAGGCTTCTACGAGGT
ATTGTAGGCCCAATGGTACTGTCGTCCTGGTTGGTATGCCAGCTCATGC
TTACTGCAATTCCGATGTTTTCAATCAAGTTGTAAAATCAATCTCCATC
GTTGGATCTTGTGTTGGAAATAGAGCTGATACAAGGGAGGCTTTAGATT
TCTTCGCCAGAGGTTTGATCAAATCTCCGATCCACTTAGCTGGCCTATC
GGATGTTCCTGAAATTTTTGCAAAGATGGAGAAGGGTGAAATTGTTGGT
AGATATGTTGTTGAGACTTCTAAATGA
SEQ ID NO 24:
S. cerevisiae GPD1
ATGTCTGCTGCTGCTGATAGATTAAACTTAACTTCCGGCCACTTGAATG
CTGGTAGAAAGAGAAGTTCCTCTTCTGTTTCTTTGAAGGCTGCCGAAAA
GCCTTTCAAGGTTACTGTGATTGGATCTGGTAACTGGGGTACTACTATT
GCCAAGGTGGTTGCCGAAAATTGTAAGGGATACCCAGAAGTTTTCGCTC
CAATAGTACAAATGTGGGTGTTCGAAGAAGAGATCAATGGTGAAAAATT
GACTGAAATCATAAATACTAGACATCAAAACGTGAAATACTTGCCTGGC
ATCACTCTACCCGACAATTTGGTTGCTAATCCAGACTTGATTGATTCAG
TCAAGGATGTCGACATCATCGTTTTCAACATTCCACATCAATTTTTGCC
CCGTATCTGTAGCCAATTGAAAGGTCATGTTGATTCACACGTCAGAGCT
ATCTCCTGTCTAAAGGGTTTTGAAGTTGGTGCTAAAGGTGTCCAATTGC
TATCCTCTTACATCACTGAGGAACTAGGTATTCAATGTGGTGCTCTATC
TGGTGCTAACATTGCCACCGAAGTCGCTCAAGAACACTGGTCTGAAACA
ACAGTTGCTTACCACATTCCAAAGGATTTCAGAGGCGAGGGCAAGGACG
TCGACCATAAGGTTCTAAAGGCCTTGTTCCACAGACCTTACTTCCACGT
TAGTGTCATCGAAGATGTTGCTGGTATCTCCATCTGTGGTGCTTTGAAG
AACGTTGTTGCCTTAGGTTGTGGTTTCGTCGAAGGTCTAGGCTGGGGTA
ACAACGCTTCTGCTGCCATCCAAAGAGTCGGTTTGGGTGAGATCATCAG
ATTCGGTCAAATGTTTTTCCCAGAATCTAGAGAAGAAACATACTACCAA
GAGTCTGCTGGTGTTGCTGATTTGATCACCACCTGCGCTGGTGGTAGAA
ACGTCAAGGTTGCTAGGCTAATGGCTACTTCTGGTAAGGACGCCTGGGA
ATGTGAAAAGGAGTTGTTGAATGGCCAATCCGCTCAAGGTTTAATTACC
```
```
TGCAAAGAAGTTCACGAATGGTTGGAAACATGTGGCTCTGTCGAAGACT
TCCCATTATTTGAAGCCGTATACCAAATCGTTTACAACAACTACCCAAT
GAAGAACCTGCCGGACATGATTGAAGAATTAGATCTACATGAAGATTAG
SEQ ID NO: 25:
S. cerevisiae GPD2
ATGCTTGCTGTCAGAAGATTAACAAGATACACATTCCTTAAGCGAACGC
ATCCGGTGTTATATACTCGTCGTGCATATAAAATTTTGCCTTCAAGATC
TACTTTCCTAAGAAGATCATTATTACAAACACAACTGCACTCAAAGATG
ACTGCTCATACTAATATCAAACAGCACAAACACTGTCATGAGGACCATC
CTATCAGAAGATCGGACTCTGCCGTGTCAATTGTACATTTGAAACGTGC
GCCCTTCAAGGTTACAGTGATTGGTTCTGGTAACTGGGGGACCACCATC
GCCAAAGTCATTGCGGAAAACACAGAATTGCATTCCCATATCTTCGAGC
CAGAGGTGAGAATGTGGGTTTTTGATGAAAAGATCGGCGACGAAAATCT
GACGGATATCATAAATACAAGACACCAGAACGTTAAATATCTACCCAAT
ATTGACCTGCCCCATAATCTAGTGGCCGATCCTGATCTTTTACACTCCA
TCAAGGGTGCTGACATCCTTGTTTTCAACATCCCTCATCAATTTTTACC
AAACATAGTCAAACAATTGCAAGGCCACGTGGCCCCTCATGTAAGGGCC
ATCTCGTGTCTAAAAGGGTTCGAGTTGGGCTCCAAGGGTGTGCAATTGC
TATCCTCCTATGTTACTGATGAGTTAGGAATCCAATGTGGCGCACTATC
TGGTGCAAACTTGGCACCGGAAGTGGCCAAGGAGCATTGGTCCGAAACC
ACCGTGGCTTACCAACTACCAAAGGATTATCAAGGTGATGGCAAGGATG
TAGATCATAAGATTTTGAAATTGCTGTTCCACAGACCTTACTTCCACGT
CAATGTCATCGATGATGTTGCTGGTATATCCATTGCCGGTGCCTTGAAG
AACGTCGTGGCACTTGCATGTGGTTTCGTAGAAGGTATGGGATGGGGTA
ACAATGCCTCCGCAGCCATTCAAAGGCTGGGTTTAGGTGAAATTATCAA
GTTCGGTAGAATGTTTTTCCCAGAATCCAAAGTCGAGACCTACTATCAA
GAATCCGCTGGTGTTGCAGATCTGATCACCACCTGCTCAGGCGGTAGAA
ACGTCAAGGTTGCCACATACATGGCCAAGACCGGTAAGTCAGCCTTGGA
AGCAGAAAAGGAATTGCTTAACGGTCAATCCGCCCAAGGGATAATCACA
TGCAGAAGTTCACGAGTGGCTACAAACATGTGAGTTGACCCAAGAAT
TCCCATTATTCGAGGCAGTCTACCAGATAGTCTACAACAACGTCCGCAT
GGAAGACCTACCGGAGATGATTGAAGAGCTAGACATCGATGACGAATAG
SEQ ID NO: 26:
S. cerevisiae GPP1
ATGCCTTTGACCACAAAACCTTTATCTTTGAAAATCAACGCCGCTCTAT
TCGATGTTGACGGTACCATCATCATCTCTCAACCAGCCATTGCTGCTTT
CTGGAGAGATTTCGGTAAAGACAAGCCTTACTTCGATGCCGAACACGTT
ATTCACATCTCTCACGGTTGGAGAACTTACGATGCCATTGCCAAGTTCG
CTCCAGACTTTGCTGATGAAGAATACGTTAACAAGCTAGAAGGTGAAAT
CCCAGAAAAGTACGGTGAACACTCCATCGAAGTTCCAGGTGCTGTCAAG
TTGTGTAATGCTTTGAACGCCTTGCCAAAGGAAAAATGGGCTGTCGCCA
CCTCTGGTACCCGTGACATGGCCAAGAAATGGTTCGACATTTTGAAGAT
```

-continued
CAAGAGACCAGAATACTTCATCACCGCCAATGATGTCAAGCAAGGTAAG

CCTCACCCAGAACCATACTTAAAGGGTAGAAACGGTTTGGGTTTCCCAA

TTAATGAACAAGACCCATCCAAATCTAAGGTTGTTGTCTTTGAAGACGC

ACCAGCTGGTATTGCTGCTGGTAAGGCTGCTGGCTGTAAAATCGTTGGT

ATTGCTACCACTTTCGATTTGGACTTCTTGAAGGAAAAGGGTTGTGACA

TCATTGTCAAGAACCACGAATCTATCAGAGTCGGTGAATACAACGCTGA

AACCGATGAAGTCGAATTGATCTTTGATGACTACTTATACGCTAAGGAT

GACTTGTTGAAATGGTAA

SEQ ID NO: 27
S. cerevisiae GPP2
ATGGGATTGACTACTAAACCTCTATCTTTGAAAGTTAACGCCGCTTTGT

TCGACGTCGACGGTACCATTATCATCTCTCAACCAGCCATTGCTGCATT

CTGGAGGGATTTCGGTAAGGACAAACCTTATTTCGATGCTGAACACGTT

ATCCAAGTCTCGCATGGTTGGAGAACGTTTGATGCCATTGCTAAGTTCG

CTCCAGACTTTGCCAATGAAGAGTATGTTAACAAATTAGAAGCTGAAAT

TCCGGTCAAGTACGGTGAAAAATCCATTGAAGTCCCAGGTGCAGTTAAG

CTGTGCAACGCTTTGAACGCTCTACCAAAAGAGAAATGGGCTGTGGCAA

CTTCCGGTACCCGTGATATGGCACAAAAATGGTTCGAGCATCTGGGAAT

CAGGAGACCAAAGTACTTCATTACCGCTAATGATGTCAAACAGGGTAAG

CCTCATCCAGAACCATATCTGAAGGGCAGGAATGGCTTAGGATATCCGA

TCAATGAGCAAGACCCTTCCAAATCTAAGGTAGTAGTATTTGAAGACGC

TCCAGCAGGTATTGCCGCCGGAAAAGCCGCCGGTTGTAAGATCATTGGT

ATTGCCACTACTTTCGACTTGGACTTCCTAAAGGAAAAAGGCTGTGACA

TCATTGTCAAAAACCACGAATCCATCAGAGTTGGCGGCTACAATGCCGA

AACAGACGAAGTTGAATTCATTTTTGACGACTACTTATATGCTAAGGAC

GATCTGTTGAAATGGTAA

SEQ ID NO: 28
dmpF ORF synthetic codon optimized
for Saccharomyces cerevisiae.
Reference sequence: Pseudomonas sp. CF600
EMBL Accession number: X60835.1
ATGAATCAGAAACTGAAAGTAGCTATCATAGGTTCCGGTAATATCGGAA

CAGACCTGATGATTAAGGTACTGCGTAATGCAAAGTACTTAGAAATGGG

CGCGATGGTCGGTATCGATGCAGCCTCTGATGGACTGGCCAGAGCTCAA

AGAATGGGCGTTACGACTACTTATGCAGGTGTAGAAGGGCTAATCAAGC

TTCCTGAATTTGCAGACATAGATTTCGTCTTCGATGCTACATCTGCATC

AGCCCACGTTCAGAACGAGGCTTTATTAAGACAAGCTAAACCTGGTATT

AGATTGATCGACCTTACCCCGGCGGCAATCGGTCCTTACTGTGTCCCCG

TAGTTAATCTCGAGGAACATTTGGGCAAGTTGAACGTTAACATGGTTAC

TTGCGGTGGCCAAGCTACTATTCCGATGGTCGCAGCTGTCTCACGTGTA

GCCAAAGTTCCATTATGCTGAGATTGTTGCTTCTATTTCAAGCAAGAGTG

CCGGACCTGGAACCAGAGCCAATATAGATGAATTCACTGAGACAACCAG

TAAAGCCATAGAAGTTATTGGTGGTGCTGCAAAGGGTAAAGCTATAATT

ATTATGAACCCAGCTGAACCACCATTGATTATGAGGGATACGGTGTATG

-continued
TGCTTTCCGCCGCCGCTGATCAAGCCGCTGTCGCAGCTTCTGTGGCTGA

AATGGTTCAAGCGGTTCAAGCATACGTGCCAGGCTATAGGTTAAAACAA

CAGGTTCAGTTTGACGTGATTCCCGAGTCCGCGCCACTAAACATCCCCG

GTTTGGGGAGATTCAGCGGGTTGAAAACAAGTGTGTTCCTAGAAGTAGA

AGGTGCTGCTCATTATTTGCCAGCATACGCAGGAAACTTAGATATTATG

ACTTCCGCAGCGTTAGCTACAGCCGAACGTATGGCGCAATCAATGTTGA

ATGCATAG

SEQ ID NO: 29
dmpF ORF
MNQKLKVAIIGSGNIGTDLMIKVLRNAKYLEMGAMVGIDAASDGLARAQ

RMGVTTTYAGVEGLIKLPEFADIDFVFDATSASAHVQNEALLRQAKPGI

RLIDLTPAAIGPYCVPVVNLEEHLGKLNVNMVTCGGQATIPMVAAVSRV

AKVHYAEIVASISSKSAGPGTRANIDEFTETTSKATEVIGGAAKGKAII

IMNPAEPPLIMRDTVYVLSAAADQAAVAASVAEMVQAVQAYVPGYRLKQ

QVQFDVIPESAPLNIPGLGRFSGLKTSVFLEVEGAAHYLPAYAGNLDIM

TSAALATAERMAQSMLNA

SEQ ID NO: 30
primer dmpF-FW
CATTGATTGCGCCATACG

SEQ ID NO: 31 primer dmpF-RV
CCGGTAATATCGGAACAGAC

SEQ ID NO: 32
Wild type sequence of dmpF gene
from Pseudomonas sp. CF600. EMBL
Accession number: X60835.1
ATGAACCAGAAACTCAAAGTCGCGATCATCGGTTCGGGCAATATCGGCA

CCGACCTGATGATCAAGGTGCTGCGCAACGCCAAGTACCTGGAAATGGG

CGCCATGGTCGGCATCGACGCCGCCTCCGACGGCCTGGCCCGCGCCCAG

CGCATGGGCGTGACGACCACCTATGCCGGCGTCGAAGGGCTGATCAAGC

TGCCCGAATTCGCCGACATCGATTTCGTCTTCGACGCCACCTCGGCCAG

TGCCCACGTGCAGAACGAGGCGCTGCTGCGCCAGGCCAAACCTGGCATC

CGCCTGATCGACCTGACCCCGGCGGCCATCGGCCCGTACTGCGTGCCGG

TGGTCAATCTGGAGGAGCACCTCGGCAAGCTCAACGTCAACATGGTTAC

CTGCGGCGGCCAGGCGACCATCCCGATGGTCGCCGCGGTCTCCCGTGTG

GCCAAGGTCCATTACGCCGAGATCGTCGCCTCGATCAGCAGCAAGTCGG

CCGGACCCGGCACCCGCGCCAACATCGACGAGTTCACCGAGACCACCAG

CAAAGCCATCGAAGTGATCGGTGGTGCGGCCAAGGGCAAGGCGATCATC

ATCATGAACCCGGCTGAGCCGCCGCTGATCATGCGCGACACCGTGTATG

TGCTGTCCGCCGCCGCCGATCAGGCCGCCGTCGCGGCCTCGGTGGCGGA

AATGGTTCAGGCGGTGCAGGCCTACGTGCCCGGCTATCGCCTGAAGCAG

CAGGTGCAGTTCGACGTGATCCCCGAGTCCGCGCCGCTGAACATCCCCG

GTCTCGGCCGGTTCAGCGGGTTGAAGACCTCGGTGTTCCTCGAAGTCGA

AGGCGCCGCCCATTACCTGCCGGCCTACGCCGGCAACCTCGACATCATG

ACCTCCGCCGCGCTGGCTACCGCCGAGCGTATGGCGCAGTCGATGTTGA

ACGCCTGA

The invention claimed is:

1. Transgenic yeast cells comprising:
   a recombinant heterologous, nucleic acid sequence encoding a protein with NAD⁺-dependent acetylating acetaldehyde dehydrogenase activity (EC 1.2.1.10),
   a nucleic acid sequence encoding a protein with NAD⁺-dependent alcohol dehydrogenase activity (EC 1.1.1.1),
   a nucleic acid sequence encoding a protein with acetyl-Coenzyme A synthetase activity (EC 6.2.1.1), and
   a nucleic acid sequence encoding a protein with NADH-dependent glycerol-3-phosphate dehydrogenase activity (EC 1.1.1.8);
   wherein the transgenic yeast cells exhibit reduced NADH-dependent glycerol synthesis in an ethanol-producing fermentation process compared to their corresponding wild-type yeast cells.

2. The transgenic yeast cells of claim 1, wherein the nucleic acid sequence encoding the protein with NAD⁺-dependent alcohol dehydrogenase activity (EC 1.1.1.1) comprises a recombinant heterologous nucleic acid sequence encoding the protein with NAD⁺-dependent alcohol dehydrogenase activity (EC 1.1.1.1).

3. The transgenic yeast cells of claim 1, wherein the nucleic acid sequence encoding the protein with NAD⁺-dependent alcohol dehydrogenase activity (EC 1.1.1.1) encodes a native protein with NAD⁺-dependent alcohol dehydrogenase activity (EC 1.1.1.1).

4. The transgenic yeast cells of claim 1, wherein the nucleic acid sequence encoding the protein with acetyl-Coenzyme A synthetase activity (EC 6.2.1.1) comprises a recombinant heterologous nucleic acid sequence encoding the protein with acetyl-Coenzyme A synthetase activity (EC 6.2.1.1).

5. The transgenic yeast cells of claim 1, wherein the nucleic acid sequence encoding the protein with acetyl-Coenzyme A synthetase activity (EC 6.2.1.1) encodes a native protein with acetyl-Coenzyme A synthetase activity (EC 6.2.1.1).

6. The transgenic yeast cells of claim 1, wherein the recombinant heterologous nucleic acid sequence encoding the protein comprising NAD⁺-dependent acetylating acetaldehyde dehydrogenase activity (EC 1.2.1.10) is operably linked to a promoter sequence selected from the group consisting of a TPI1 promoter sequence, a glyceraldehyde-3-phosphate dehydrogenase TDH3 promoter sequence, a translational elongation factor EF-1 alpha TEF1 promoter sequence, an alcohol dehydrogenase ADH1 promoter sequence, a glucose-6-phosphate dehydrogenase promoter sequence, a protease promoter sequence, a glucoamylase promoter sequence, an amylase promoter sequence, a catalase promoter sequence, a glucose oxidase promoter sequence, a beta-galacatosidase lacA promoter sequence, an alpha-glucosidase aglA promoter sequence, a xylanase promoter sequence, and a cellulose promoter sequence.

7. The transgenic yeast cells of claim 6, wherein the promoter sequence is selected from the group consisting of a triosephosphate dehydrogenase TPI1 promoter sequence, a glyceraldehyde-3-phosphate dehydrogenase TDH3 promoter sequence, an alcohol dehydrogenase ADH1 promoter sequence, and a glucose-6-phosphate dehydrogenase promoter sequence.

8. The transgenic yeast cells of claim 1, wherein the recombinant heterologous nucleic acid sequence encoding the nucleic acid sequence encoding a protein with NAD⁺-dependent alcohol dehydrogenase activity (EC 1.1.1.1) is operably linked to a promoter sequence selected from the group consisting of a TPI1 promoter sequence, a glyceraldehyde-3-phosphate dehydrogenase TDH3 promoter sequence, a translational elongation factor EF-1 alpha TEF1 promoter sequence, an alcohol dehydrogenase ADH1 promoter sequence, a glucose-6-phosphate dehydrogenase promoter sequence, a protease promoter sequence, a glucoamylase promoter sequence, an amylase promoter sequence, a catalase promoter sequence, a glucose oxidase promoter sequence, a beta-galacatosidase lacA promoter sequence, an alpha-glucosidase aglA promoter sequence, a xylanase promoter sequence, and a cellulose promoter sequence.

9. The transgenic yeast cells of claim 8, wherein the promoter sequence is selected from the group consisting of a triosephosphate dehydrogenase TPI1 promoter sequence, a glyceraldehyde-3-phosphate dehydrogenase TDH3 promoter sequence, an alcohol dehydrogenase ADH1 promoter sequence, and a glucose-6-phosphate dehydrogenase promoter sequence.

10. The transgenic yeast cells of claim 1, wherein the yeast cells comprise multiple copies of the recombinant heterologous nucleic acid sequence encoding the protein with NAD⁺-dependent acetylating acetaldehyde dehydrogenase activity (EC 1.2.1.10).

11. The transgenic yeast cells of claim 1, wherein the yeast cells comprise multiple copies of the recombinant heterologous nucleic acid sequence encoding the protein with NAD⁺-dependent alcohol dehydrogenase activity (EC 1.1.1.1).

12. The transgenic yeast cells of claim 1, wherein the yeast cells comprise multiple copies of the recombinant heterologous nucleic acid sequence encoding the protein with NAD⁺-dependent acetylating acetaldehyde dehydrogenase activity (EC 1.2.1.10), and multiple copies of the recombinant heterologous nucleic acid sequence encoding the protein with NAD⁺-dependent alcohol dehydrogenase activity (EC 1.1.1.1).

13. The transgenic yeast cells of claim 1, further comprising a genomic mutation in at least one gene selected from the group consisting of GPD1 and GPD2.

14. The transgenic yeast cells of claim 13, wherein the genomic mutation comprises a mutation in the gene sequence that encodes a gpd1 enzyme.

15. The transgenic yeast cells of claim 13, wherein the genomic mutation comprises a mutation in the gene sequence that encodes a gpd2 enzyme.

16. The transgenic yeast cells of claim 13, wherein the genomic mutation comprises a mutation in the GPD1 promoter sequence.

17. The transgenic yeast cells of claim 13, wherein the genomic mutation comprises a mutation in the GPD2 promoter sequence.

18. A method of producing ethanol from a fermentable carbohydrate comprising culturing the transgenic yeast cells of claim 1 under anaerobic conditions.

19. The method of claim 18, wherein the fermentable carbohydrate is glucose.

20. Transgenic S. cerevisiae yeast cells comprising:
a recombinant heterologous, nucleic acid sequence encoding a protein with $NAD^+$-dependent acetylating acetaldehyde dehydrogenase activity (EC 1.2.1.10),
a nucleic acid sequence encoding a protein with $NAD^+$-dependent alcohol dehydrogenase activity (EC 1.1.1.1),
a nucleic acid sequence encoding a protein with acetyl-Coenzyme A synthetase activity (EC 6.2.1.1), and
a nucleic acid sequence encoding a protein with NADH-dependent glycerol-3-phosphate dehydrogenase activity (EC 1.1.1.8);
wherein the transgenic yeast cells exhibit reduced NADH-dependent glycerol synthesis in an ethanol-producing fermentation process compared to their corresponding wild-type yeast cells.

21. The transgenic yeast cells of claim 20, wherein the nucleic acid sequence encoding the protein with $NAD^+$-dependent alcohol dehydrogenase activity (EC 1.1.1.1) comprises a recombinant heterologous nucleic acid sequence encoding the protein with $NAD^+$-dependent alcohol dehydrogenase activity (EC 1.1.1.1).

22. The transgenic yeast cells of claim 20, wherein the nucleic acid sequence encoding the protein with $NAD^+$-dependent alcohol dehydrogenase activity (EC 1.1.1.1) is encodes a native protein with $NAD^+$-dependent alcohol dehydrogenase activity (EC 1.1.1.1).

23. The transgenic yeast cells of claim 20, wherein the nucleic acid sequence encoding the protein with acetyl-Coenzyme A synthetase activity (EC 6.2.1.1) comprises a recombinant heterologous nucleic acid sequence encoding the protein with acetyl-Coenzyme A synthetase activity (EC 6.2.1.1).

24. The transgenic yeast cells of claim 20, wherein the nucleic acid sequence encoding the protein with acetyl-Coenzyme A synthetase activity (EC 6.2.1.1) encodes a native protein with acetyl-Coenzyme A synthetase activity (EC 6.2.1.1).

25. The transgenic yeast cells of claim 20, wherein the recombinant heterologous nucleic acid sequence encoding the protein comprising $NAD^+$-dependent acetylating acetaldehyde dehydrogenase activity (EC 1.2.1.10) is operably linked to a promoter sequence selected from the group consisting of a TPI1 promoter sequence, a glyceraldehyde-3-phosphate dehydrogenase TDH3 promoter sequence, a translational elongation factor EF-1 alpha TEF1 promoter sequence, an alcohol dehydrogenase ADH1 promoter sequence, a glucose-6-phosphate dehydrogenase promoter sequence, a protease promoter sequence, a glucoamylase promoter sequence, an amylase promoter sequence, a catalase promoter sequence, a glucose oxidase promoter sequence, a beta-galacatosidase lacA promoter sequence, an alpha-glucosidase aglA promoter sequence, a xylanase promoter sequence, and a cellulose promoter sequence.

26. The transgenic yeast cells of claim 25, wherein the promoter sequence is selected from the group consisting of a triosephosphate dehydrogenase TPI1 promoter sequence, a glyceraldehyde-3-phosphate dehydrogenase TDH3 promoter sequence, an alcohol dehydrogenase ADH1 promoter sequence, and a glucose-6-phosphate dehydrogenase promoter sequence.

27. The transgenic yeast cells of claim 20, wherein the nucleic acid sequence encoding a protein with $NAD^+$-dependent alcohol dehydrogenase activity (EC 1.1.1.1) is operably linked to a promoter sequence selected from the group consisting of a TPI1 promoter sequence, a glyceraldehyde-3-phosphate dehydrogenase TDH3 promoter sequence, a translational elongation factor EF-1 alpha TEF1 promoter sequence, an alcohol dehydrogenase ADH1 promoter sequence, a glucose-6-phosphate dehydrogenase promoter sequence, a protease promoter sequence, a glucoamylase promoter sequence, an amylase promoter sequence, a catalase promoter sequence, a glucose oxidase promoter sequence, a beta-galacatosidase lacA promoter sequence, an alpha-glucosidase aglA promoter sequence, a xylanase promoter sequence, and a cellulose promoter sequence.

28. The transgenic yeast cells of claim 27, wherein the promoter sequence is selected from the group consisting of a triosephosphate dehydrogenase TPI1 promoter sequence, a glyceraldehyde-3-phosphate dehydrogenase TDH3 promoter sequence, an alcohol dehydrogenase ADH1 promoter sequence, and a glucose-6-phosphate dehydrogenase promoter sequence.

29. A method of producing ethanol from a fermentable carbohydrate comprising culturing the transgenic yeast cells of claim 20 under anaerobic conditions.

30. The method of claim 29, wherein the fermentable carbohydrate is glucose.

\* \* \* \* \*